US 8,105,357 B2

(12) United States Patent
Bruneau et al.

(10) Patent No.: US 8,105,357 B2
(45) Date of Patent: Jan. 31, 2012

(54) INTERSPINOUS PROCESS BRACE

(75) Inventors: Aurelien Bruneau, Memphis, TN (US);
Kent M. Anderson, Memphis, TN (US);
Roy Lim, Memphis, TN (US); Eric C. Lange, Collierville, TN (US); Thomas Carls, Memphis, TN (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1047 days.

(21) Appl. No.: 11/414,060

(22) Filed: Apr. 28, 2006

(65) Prior Publication Data
US 2007/0270828 A1 Nov. 22, 2007

(51) Int. Cl.
*A61B 17/70* (2006.01)

(52) U.S. Cl. .................. 606/248; 606/90; 623/17.11

(58) Field of Classification Search .......... 606/248–249, 606/263, 232–233, 90, 247; 602/12; 600/233; 623/17.11–17.16
See application file for complete search history.

(56) References Cited

U.S. PATENT DOCUMENTS

| 278,097 A | 5/1883 | Collins |
| 1,706,431 A | 3/1929 | Whitliff |
| 2,502,902 A | 4/1950 | Tofflemire |
| 2,677,369 A | 5/1954 | Knowles |
| 3,123,077 A | 3/1964 | Alcamo |
| 3,397,699 A | 8/1968 | Kohl |
| 3,648,691 A | 3/1972 | Lumb et al. |
| 3,654,668 A | 4/1972 | Appleton |
| 3,678,542 A | 7/1972 | Prete, Jr. |
| 4,003,376 A | 1/1977 | McKay et al. |
| 4,011,602 A | 3/1977 | Rybicki et al. |
| 4,047,523 A | 9/1977 | Hall |
| 4,078,559 A | 3/1978 | Nissinen |
| 4,257,409 A | 3/1981 | Bacal et al. |
| 4,327,736 A | 5/1982 | Inoue |
| 4,448,191 A | 5/1984 | Rodnyansky et al. |
| 4,554,914 A | 11/1985 | Kapp et al. |
| 4,570,618 A | 2/1986 | Wu |
| 4,573,454 A | 3/1986 | Hoffman |
| 4,604,995 A | 8/1986 | Stephens et al. |
| 4,643,174 A | 2/1987 | Horiuchi |
| 4,643,178 A | 2/1987 | Nastari et al. |
| 4,686,970 A | 8/1987 | Dove |
| 4,721,103 A | 1/1988 | Freedland |
| 4,776,851 A | 10/1988 | Bruchman et al. |

(Continued)

FOREIGN PATENT DOCUMENTS

DE  2821678 A1  11/1979

(Continued)

OTHER PUBLICATIONS

Merriam-Webster, definition of "integral", accessed at http://www.merriam-webster.com on Feb. 2, 2010.*

(Continued)

*Primary Examiner* — Eduardo C Robert
*Assistant Examiner* — Julianna N Harvey

(57) ABSTRACT

An intervertebral process brace is disclosed and can include a frame that can support a first vertebral process and a second vertebral process. The intervertebral process brace can also include a first vertebral process support strap that can span a first portion of the frame. The first vertebral process support strap can engage the first vertebral process and bind the first vertebral process between the first vertebral process support strap and the first portion of the frame.

8 Claims, 16 Drawing Sheets

U.S. PATENT DOCUMENTS

| | | | |
|---|---|---|---|
| 4,779,816 A | 10/1988 | Varlet | |
| 4,827,918 A | 5/1989 | Olerud | |
| 4,841,959 A | 6/1989 | Ransford | |
| 4,936,848 A | 6/1990 | Bagby | |
| 4,998,936 A | 3/1991 | Mehdian | |
| 5,011,484 A | 4/1991 | Breard | |
| 5,030,220 A * | 7/1991 | Howland | 606/261 |
| 5,047,055 A | 9/1991 | Bao et al. | |
| 5,092,866 A | 3/1992 | Breard et al. | |
| 5,180,393 A | 1/1993 | Commarmond | |
| 5,201,734 A | 4/1993 | Cozad et al. | |
| 5,236,460 A | 8/1993 | Barber | |
| 5,242,444 A | 9/1993 | MacMillan | |
| 5,306,275 A | 4/1994 | Bryan | |
| 5,314,477 A | 5/1994 | Marnay | |
| 5,316,422 A | 5/1994 | Coffman | |
| 5,356,412 A | 10/1994 | Golds et al. | |
| 5,356,417 A | 10/1994 | Golds | |
| 5,360,430 A | 11/1994 | Lin | |
| 5,366,455 A | 11/1994 | Dove | |
| 5,395,374 A | 3/1995 | Miller et al. | |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,527,312 A | 6/1996 | Ray | |
| 5,571,189 A | 11/1996 | Kuslich | |
| 5,575,819 A | 11/1996 | Amis | |
| 5,609,634 A | 3/1997 | Voydeville | |
| 5,628,756 A | 5/1997 | Barker, Jr. et al. | |
| 5,645,599 A | 7/1997 | Samani | |
| 5,665,096 A | 9/1997 | Yoon | |
| 5,665,122 A | 9/1997 | Kambin | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,725,582 A | 3/1998 | Bevan et al. | |
| 5,755,797 A | 5/1998 | Baumgartner | |
| 5,797,916 A | 8/1998 | McDowell | |
| 5,810,815 A | 9/1998 | Morales | |
| 5,836,948 A | 11/1998 | Zucherman et al. | |
| 5,860,977 A | 1/1999 | Zucherman et al. | |
| 5,885,290 A | 3/1999 | Guerrero et al. | |
| 5,976,186 A | 11/1999 | Bao et al. | |
| 6,019,792 A | 2/2000 | Cauthen | |
| 6,022,376 A | 2/2000 | Assell et al. | |
| 6,048,342 A | 4/2000 | Zucherman et al. | |
| 6,066,154 A | 5/2000 | Reiley et al. | |
| 6,068,630 A | 5/2000 | Zucherman et al. | |
| 6,074,390 A | 6/2000 | Zucherman et al. | |
| 6,090,043 A * | 7/2000 | Austin et al. | 600/217 |
| 6,132,464 A | 10/2000 | Martin | |
| 6,179,874 B1 | 1/2001 | Cauthen | |
| 6,214,037 B1 | 4/2001 | Mitchell et al. | |
| 6,238,397 B1 | 5/2001 | Zucherman et al. | |
| 6,277,120 B1 | 8/2001 | Lawson | |
| 6,293,949 B1 | 9/2001 | Justis et al. | |
| 6,299,613 B1 | 10/2001 | Ogilvie et al. | |
| 6,312,431 B1 | 11/2001 | Asfora | |
| 6,332,894 B1 | 12/2001 | Stalcup et al. | |
| 6,336,930 B1 | 1/2002 | Stalcup et al. | |
| 6,352,537 B1 | 3/2002 | Strnad | |
| 6,364,883 B1 | 4/2002 | Santilli | |
| 6,395,034 B1 | 5/2002 | Suddaby | |
| 6,402,750 B1 | 6/2002 | Atkinson et al. | |
| 6,402,785 B1 | 6/2002 | Zdeblick et al. | |
| 6,419,703 B1 | 7/2002 | Fallin et al. | |
| 6,419,704 B1 | 7/2002 | Ferree | |
| 6,425,923 B1 | 7/2002 | Stalcup et al. | |
| 6,440,168 B1 | 8/2002 | Cauthen | |
| 6,440,169 B1 | 8/2002 | Elberg et al. | |
| 6,447,514 B1 | 9/2002 | Stalcup et al. | |
| 6,451,019 B1 | 9/2002 | Zucherman et al. | |
| 6,500,178 B2 | 12/2002 | Zucherman et al. | |
| 6,511,508 B1 | 1/2003 | Shahinpoor et al. | |
| 6,514,256 B2 | 2/2003 | Zucherman et al. | |
| 6,558,390 B2 | 5/2003 | Cragg | |
| 6,582,433 B2 | 6/2003 | Yun | |
| 6,626,944 B1 | 9/2003 | Taylor | |
| 6,645,207 B2 | 11/2003 | Dixon et al. | |
| 6,645,248 B2 | 11/2003 | Casutt | |
| 6,669,729 B2 | 12/2003 | Chin | |
| 6,695,842 B2 | 2/2004 | Zucherman et al. | |
| 6,699,246 B2 | 3/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 * | 7/2004 | Senegas | 606/249 |
| 6,805,697 B1 | 10/2004 | Helm et al. | |
| 6,835,205 B2 | 12/2004 | Atkinson et al. | |
| 6,852,128 B2 | 2/2005 | Lange | |
| 6,863,688 B2 | 3/2005 | Ralph et al. | |
| 6,899,713 B2 | 5/2005 | Shaolian et al. | |
| 6,902,580 B2 | 6/2005 | Fallin et al. | |
| 6,946,000 B2 | 9/2005 | Senegas et al. | |
| 6,958,077 B2 | 10/2005 | Suddaby | |
| 6,969,405 B2 | 11/2005 | Suddaby | |
| 6,972,036 B2 | 12/2005 | Boehm, Jr. et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,097,654 B1 | 8/2006 | Freedland | |
| 7,101,375 B2 | 9/2006 | Zucherman et al. | |
| 7,105,024 B2 | 9/2006 | Richelsoph | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,367,978 B2 | 5/2008 | Drewry et al. | |
| 7,377,942 B2 | 5/2008 | Berry | |
| 7,442,208 B2 | 10/2008 | Mathieu et al. | |
| 7,445,637 B2 | 11/2008 | Taylor | |
| 7,458,981 B2 | 12/2008 | Fielding et al. | |
| 7,524,324 B2 | 4/2009 | Winslow et al. | |
| 7,604,652 B2 | 10/2009 | Arnin et al. | |
| 7,658,752 B2 | 2/2010 | Labrom et al. | |
| 7,749,252 B2 | 7/2010 | Zucherman et al. | |
| 7,771,456 B2 | 8/2010 | Hartmann et al. | |
| 7,842,072 B2 | 11/2010 | Dawson | |
| 7,862,615 B2 | 1/2011 | Carli et al. | |
| 7,901,430 B2 | 3/2011 | Matsuura et al. | |
| 2001/0016743 A1 | 8/2001 | Zucherman et al. | |
| 2002/0029039 A1 | 3/2002 | Zucherman et al. | |
| 2002/0133155 A1 | 9/2002 | Ferree | |
| 2002/0143331 A1 | 10/2002 | Zucherman et al. | |
| 2002/0147449 A1 * | 10/2002 | Yun | 606/61 |
| 2002/0188297 A1 | 12/2002 | Dakin et al. | |
| 2003/0040746 A1 | 2/2003 | Mitchell et al. | |
| 2003/0045940 A1 | 3/2003 | Eberlein et al. | |
| 2003/0065330 A1 | 4/2003 | Zucherman et al. | |
| 2003/0139814 A1 | 7/2003 | Bryan | |
| 2003/0153915 A1 | 8/2003 | Nekozuka et al. | |
| 2003/0220649 A1 | 11/2003 | Bao et al. | |
| 2004/0055607 A1 | 3/2004 | Boehm, Jr. et al. | |
| 2004/0083002 A1 | 4/2004 | Belef et al. | |
| 2004/0097931 A1 | 5/2004 | Mitchell | |
| 2004/0106995 A1 | 6/2004 | Le Couedic et al. | |
| 2004/0117017 A1 | 6/2004 | Pasquet et al. | |
| 2004/0127907 A1 | 7/2004 | Dakin et al. | |
| 2004/0133280 A1 | 7/2004 | Trieu | |
| 2004/0186475 A1 | 9/2004 | Falahee | |
| 2004/0186576 A1 | 9/2004 | Biscup et al. | |
| 2004/0199255 A1 | 10/2004 | Mathieu et al. | |
| 2004/0215342 A1 | 10/2004 | Suddaby | |
| 2004/0225360 A1 | 11/2004 | Malone | |
| 2004/0230305 A1 | 11/2004 | Gorensek et al. | |
| 2005/0010293 A1 | 1/2005 | Zucherman et al. | |
| 2005/0033431 A1 | 2/2005 | Gordon et al. | |
| 2005/0033432 A1 | 2/2005 | Gordon et al. | |
| 2005/0033434 A1 | 2/2005 | Berry | |
| 2005/0033437 A1 | 2/2005 | Bao et al. | |
| 2005/0033439 A1 | 2/2005 | Gordon et al. | |
| 2005/0038432 A1 | 2/2005 | Shaolian et al. | |
| 2005/0049708 A1 | 3/2005 | Atkinson et al. | |
| 2005/0101955 A1 | 5/2005 | Zucherman et al. | |
| 2005/0143738 A1 | 6/2005 | Zucherman et al. | |

| | | |
|---|---|---|
| 2005/0165398 A1 | 7/2005 | Reiley |
| 2005/0197702 A1 | 9/2005 | Coppes et al. |
| 2005/0203512 A1 | 9/2005 | Hawkins et al. |
| 2005/0203624 A1 | 9/2005 | Serhan et al. |
| 2005/0203626 A1 | 9/2005 | Sears et al. |
| 2005/0209603 A1 | 9/2005 | Zucherman et al. |
| 2005/0209696 A1 | 9/2005 | Lin et al. |
| 2005/0216017 A1 | 9/2005 | Fielding et al. |
| 2005/0228391 A1 | 10/2005 | Levy et al. |
| 2005/0240267 A1 | 10/2005 | Randall et al. |
| 2005/0261768 A1 | 11/2005 | Trieu |
| 2005/0267579 A1 | 12/2005 | Reiley et al. |
| 2005/0267580 A1 | 12/2005 | Suddaby |
| 2005/0273110 A1 | 12/2005 | Boehm, Jr. et al. |
| 2005/0288672 A1 | 12/2005 | Feree |
| 2006/0004367 A1 | 1/2006 | Alamin et al. |
| 2006/0004447 A1 | 1/2006 | Mastrorio et al. |
| 2006/0015181 A1 | 1/2006 | Elberg |
| 2006/0015183 A1 | 1/2006 | Gilbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1 | 6/2006 | Taylor |
| 2006/0149242 A1 | 7/2006 | Kraus et al. |
| 2006/0149278 A1 | 7/2006 | Abdou |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235386 A1 | 10/2006 | Anderson |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241610 A1* | 10/2006 | Lim et al. ................ 606/69 |
| 2006/0241613 A1 | 10/2006 | Brueneau et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0088436 A1 | 4/2007 | Parsons et al. |
| 2007/0100340 A1 | 5/2007 | Lange et al. |
| 2007/0123861 A1 | 5/2007 | Dewey et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276496 A1 | 11/2007 | Lange et al. |
| 2007/0276497 A1 | 11/2007 | Anderson |
| 2008/0009866 A1 | 1/2008 | Alamin et al. |
| 2008/0015693 A1 | 1/2008 | Le Couedic |
| 2008/0021457 A1 | 1/2008 | Anderson et al. |
| 2008/0021460 A1 | 1/2008 | Bruneau et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0195152 A1 | 8/2008 | Altarac et al. |
| 2008/0215094 A1 | 9/2008 | Taylor |
| 2008/0281360 A1 | 11/2008 | Vittur et al. |
| 2008/0281361 A1 | 11/2008 | Vittur et al. |
| 2009/0018658 A1 | 1/2009 | Garcia |
| 2009/0062915 A1 | 3/2009 | Kohm et al. |
| 2009/0105773 A1 | 4/2009 | Lange et al. |
| 2009/0240283 A1 | 9/2009 | Carls et al. |
| 2009/0270918 A1 | 10/2009 | Attias et al. |
| 2010/0121379 A1 | 5/2010 | Edmond |
| 2010/0204732 A1 | 8/2010 | Aschmann et al. |
| 2010/0211101 A1 | 8/2010 | Blackwell et al. |

FOREIGN PATENT DOCUMENTS

| | | |
|---|---|---|
| DE | 101 49 385 A1 | 4/2003 |
| DE | 202006018978 U1 | 2/2007 |
| EP | 0418387 A1 | 3/1991 |
| EP | 0322334 B1 | 2/1992 |
| EP | 0 661 957 B1 | 9/1998 |
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A | 3/1993 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A | 1/1996 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799640 A | 4/2001 |
| FR | 2799948 A1 | 4/2001 |
| FR | 2816197 A1 | 5/2002 |
| FR | 2851154 A | 8/2004 |

| | | |
|---|---|---|
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 91/13598 | 9/1991 |
| WO | WO 94/26192 | 11/1994 |
| WO | WO 94/26195 | 11/1994 |
| WO | WO 98/20939 | 5/1998 |
| WO | WO 98/34568 | 8/1998 |
| WO | WO 00/45752 | 8/2000 |
| WO | WO 01/15638 A1 | 3/2001 |
| WO | WO 02/09625 A1 | 2/2002 |
| WO | WO 03/007829 | 1/2003 |
| WO | WO 2004/028401 A2 | 4/2004 |
| WO | WO 2004/047691 A1 | 6/2004 |
| WO | WO 2004073533 A1 * | 9/2004 |
| WO | 2004/084743 A1 | 10/2004 |
| WO | 2004/084768 A | 10/2004 |
| WO | 2005/002474 A | 1/2005 |
| WO | 2005/009300 A | 2/2005 |
| WO | WO 2005/009300 A1 | 2/2005 |
| WO | WO 2005/016194 A2 | 2/2005 |
| WO | WO 2005/037150 A1 | 4/2005 |
| WO | WO 2005/044118 A1 | 5/2005 |
| WO | WO 2005/097004 A2 | 10/2005 |
| WO | WO 2005/110258 A1 | 11/2005 |
| WO | WO 2005/115261 A1 | 12/2005 |
| WO | WO 2006/009855 A2 | 1/2006 |
| WO | 2006/025815 A | 3/2006 |
| WO | 2006/044786 A | 4/2006 |
| WO | WO 2006/064356 A1 | 6/2006 |
| WO | 2006/089085 A | 8/2006 |
| WO | WO 2007/034516 A1 | 3/2007 |
| WO | 2007/075788 A | 7/2007 |

OTHER PUBLICATIONS

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertebral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertebral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

Anasetti et al., "Spine Stability After Implantation Of An Interspinous Device: An In Vitro And Finite Element Biomechanical Study," J. Neurosurg. Spine, Nov. 2010, vol. 13, pp. 568-575.

Bellini et al., "Biomechanics Of The Lumbar Spine After Dynamic Stabilization," J. Spinal Discord Tech., 2006, vol. 00, No. 00, pp. 1-7.

Bu Ric et al., "Diam Device For Low Back Pain In Degenerative Disc Disease 24 Months Follow-up," Advances in Minimally Invasive Surgery And Therapy For Spine And Nerves, Alexandre et al., eds., 2011, pp. 177-182, Spinger-Verlat/Wien.

Phillips et al., "Biomechanics Of Posterior Dynamic Stabiling Device (DIAM) After Facetectomy And Disectomy," The Spine Journal, 2006, vol. 6, pp. 714-722.

Taylor et al., "Device For Intervertebral Assisted Motion: Technique And Intial Results," 22 Neurosurg. Focus, Jan. 2007, vol. 22, No. 1, pp. 1-6.

Wilke et al., "Biomedical Effect Of Different Lumbar Interspinous Implants On Flexibilty And Intradiscal Pressure," Eur Spine J., Vo. 17, published online Jun. 27, 2008, pp. 1049-1056.

Zhao et al., "Efficacy Of The Dynamic Interspinous Assisted Motion System In Clinical Treatment Of Degenerative Lumbar Disease," Chin. Med. J., 2010, vol. 123, No. 21, pp. 2974-2977.

* cited by examiner

INTERSPINOUS PROCESS BRACE

FIELD OF THE DISCLOSURE

The present disclosure relates generally to orthopedics and orthopedic surgery. More specifically, the present disclosure relates to devices used to support adjacent spinous processes.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

Figure 1:
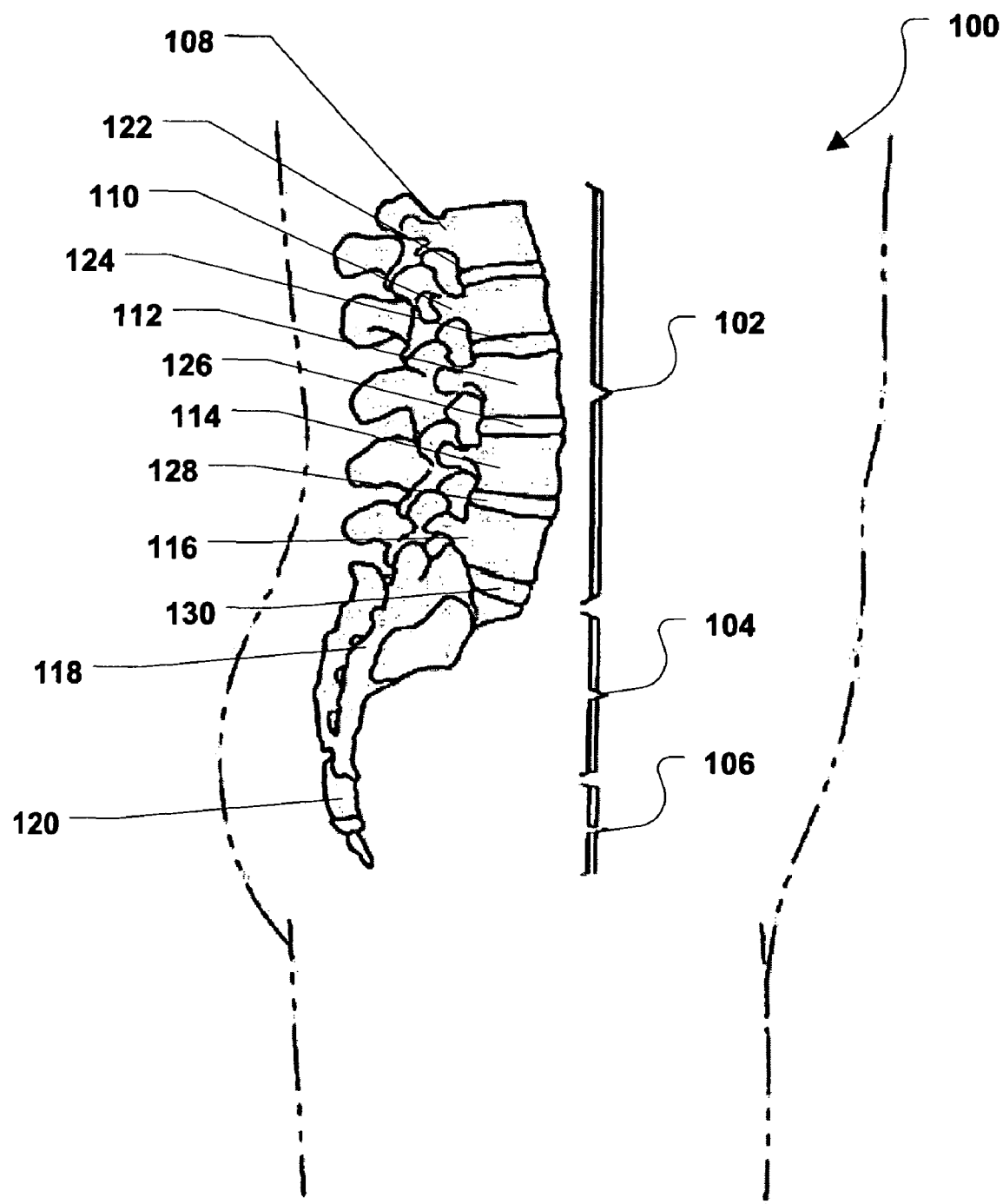
FIG. 1 is a lateral view of a portion of a vertebral column.

An intervertebral process brace is disclosed and can include a frame that can support a first vertebral process and a second vertebral process. The intervertebral process brace can also include a first vertebral process support strap that can span a first portion of the frame. The first vertebral process support strap can engage the first vertebral process and bind the first vertebral process between the first vertebral process support strap and the first portion of the frame.

In another embodiment, a method of treating a spine is disclosed and can include installing an intervertebral process brace around a first vertebral process and a second vertebral process. The intervertebral process brace can include a first vertebral process support strap and a second vertebral support strap. Further, the method can include tightening the first vertebral process support strap at least partially around the first vertebral process.

In yet another embodiment, a method of treating a spine is disclosed and can include installing an intervertebral process brace around a first vertebral process and a second vertebral process. The intervertebral process brace can include a vertebral process support strap and a vertebral process bracket. The method can also include tightening the vertebral process support strap to increase a distance between the first vertebral process and the second vertebral process.

In still another embodiment, an interspinous process brace is disclosed and can include a frame that can be installed around a first spinous process and a second spinous process. The interspinous process brace can also include a first spinous process support strap that can span a first portion of the frame. Further, the interspinous process brace can include a second spinous process support strap that can span a second portion of the frame. The first spinous process support strap and the second spinous support strap can be moved relative to the frame to increase a distance between the first spinous process and the second spinous process.

In yet still another embodiment, an interspinous process brace is disclosed and can include a frame that can be installed around a first spinous process and a second spinous process. The interspinous process brace can also include a spinous process support strap that can span a portion of the frame. Also, the interspinous process brace can include a spinous process support bracket that can extend from the frame. The spinous process support strap can be moved relative to the frame to increase a distance between the first spinous process and the second spinous process.

In another embodiment, a brace is disclosed and can include a frame configured to support a first hard tissue body and a second hard tissue body in a relative spatial relationship. Moreover, the brace can include a first support strap that can span a first portion of the frame. The first support strap can be configured to engage the first hard tissue body and bind the first hard tissue body between the first support strap and the first portion of the frame.

Description of Relevant Anatomy

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
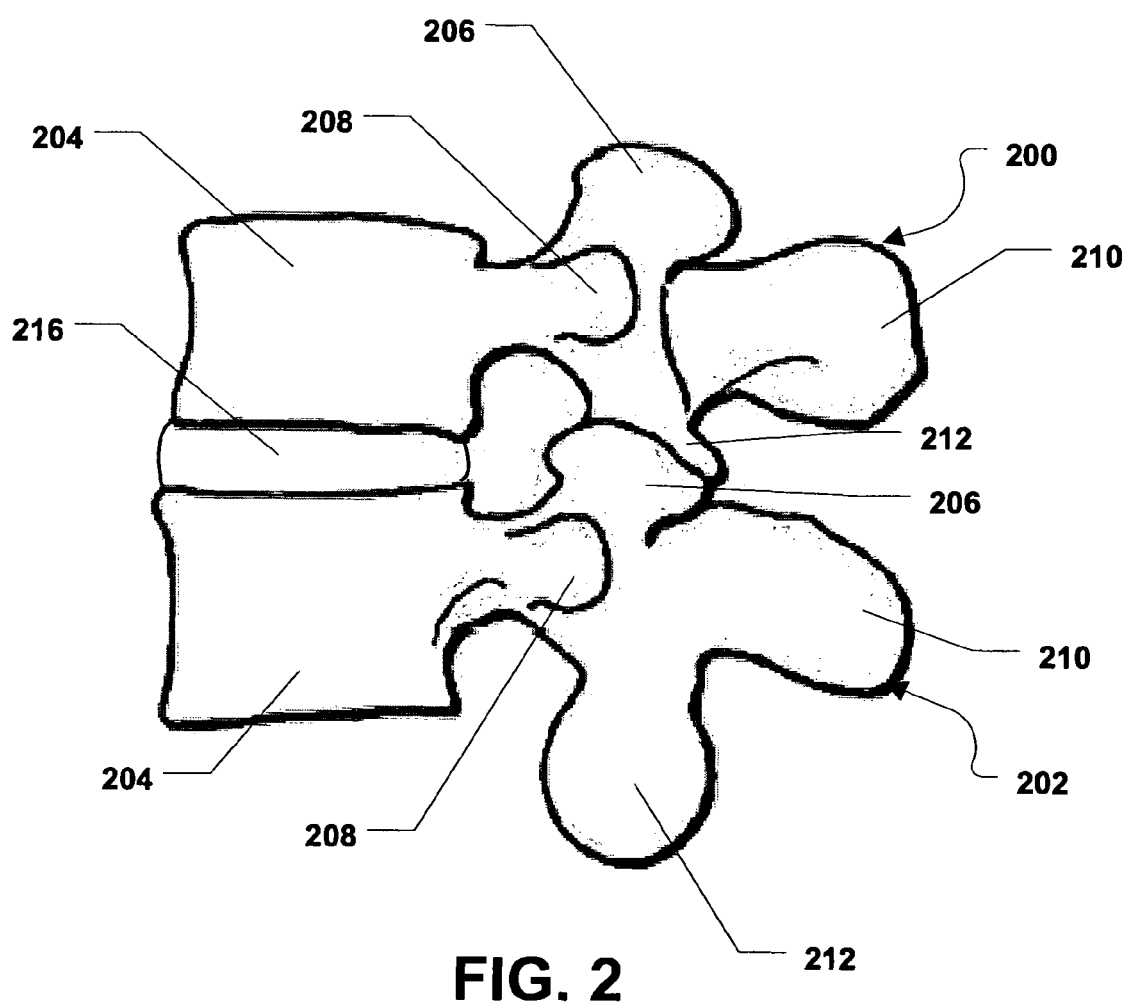
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
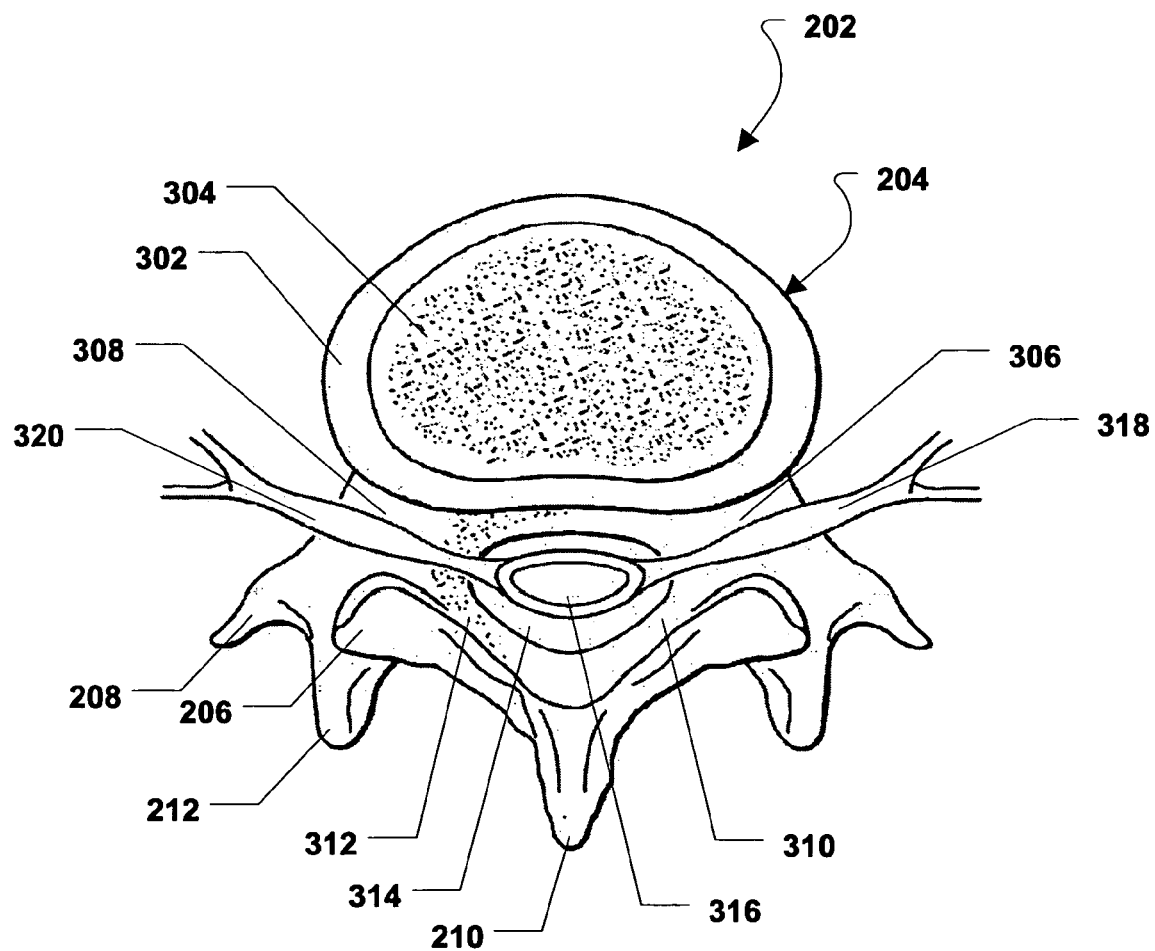
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a First Embodiment of an Interspinous Process Brace

Figure 4:
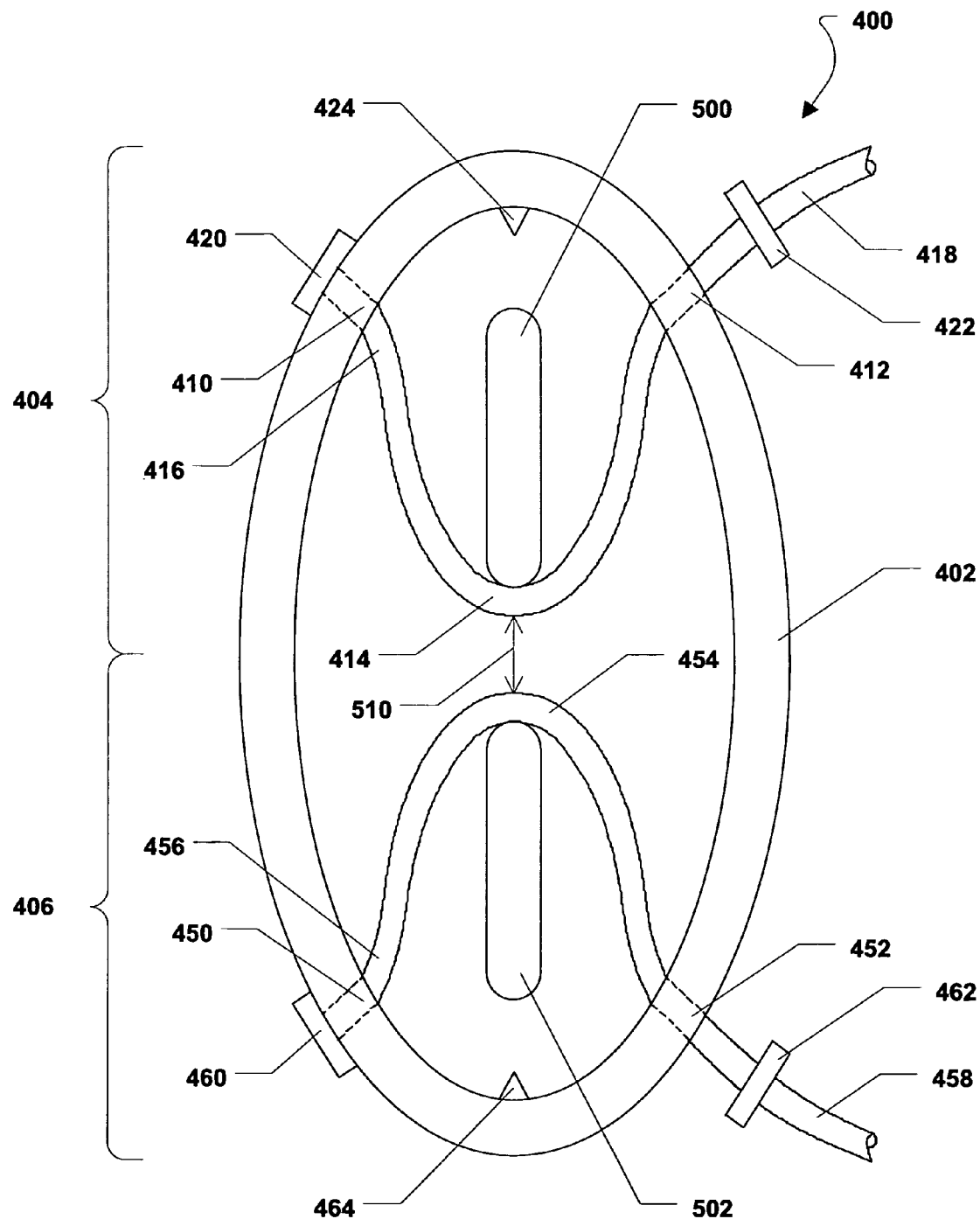
FIG. 4 is a plan view of a first interspinous process brace in a relaxed configuration.
Figure 5:
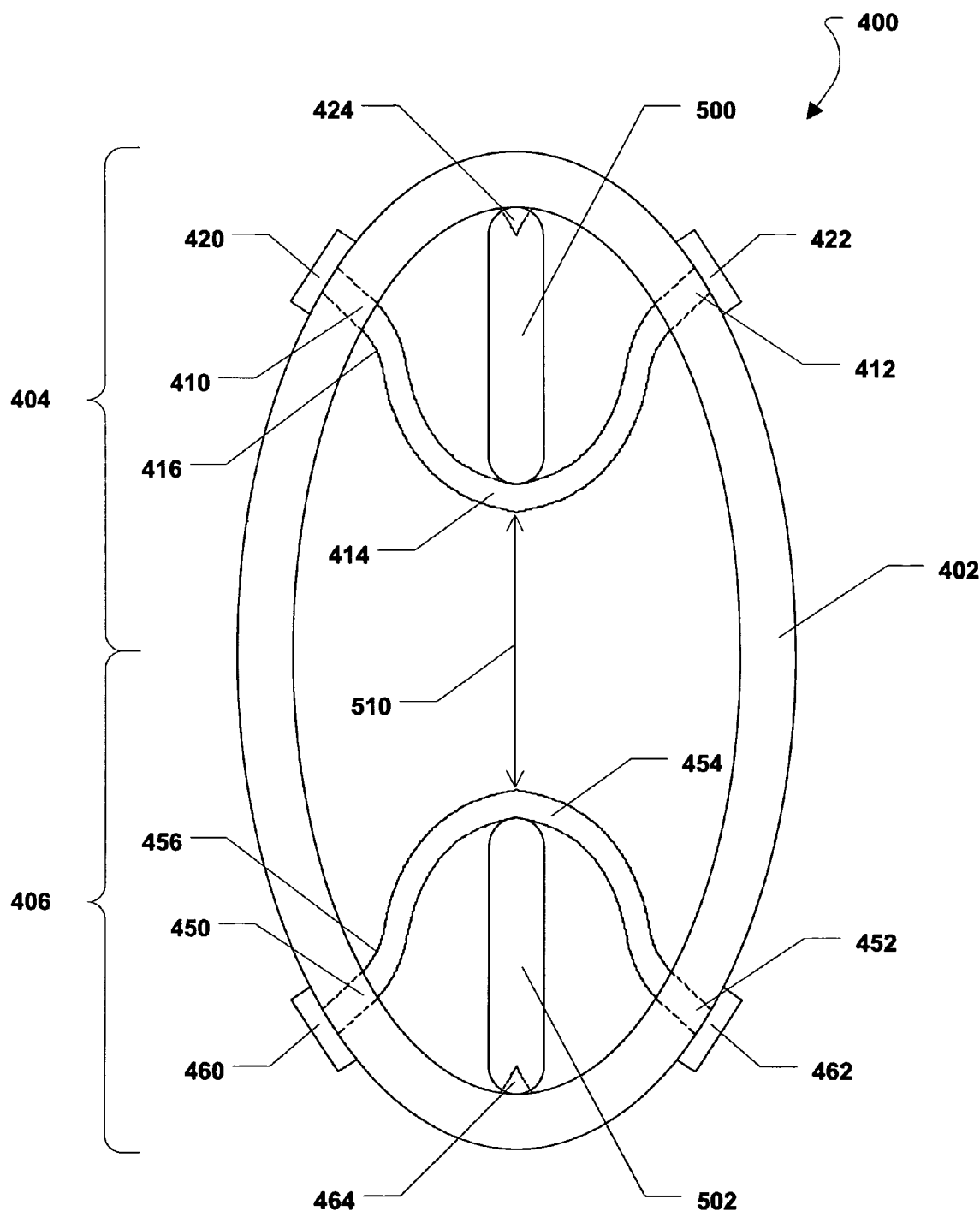
FIG. 5 is a plan view of the first interspinous process brace in a taut configuration.

Referring to FIG. 4 and FIG. 5, a first interspinous process brace is shown and is generally designated 400. As shown, the adjustable interspinous process brace 400 can include a generally ellipse-shaped frame 402 that can include a superior portion 404 and an inferior portion 406. In a particular embodiment, the frame 402 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the frame 402 can be made from any other substantially rigid biocompatible materials.

As illustrated in FIG. 4 and FIG. 5, the superior portion 404 of the frame 402 can include a first hole 410 and a second hole 412. A superior spinous process support strap 414 can be inserted through the first hole 410 and the second hole 412 and can span the superior portion 404 of the frame 402. The superior spinous process support strap 414 can include a proximal end 416 and a distal end 418. A first superior locking collar 420 can engage the proximal end 416 of the superior spinous process support strap 414 and prevent the proximal end 416 of the superior spinous process support strap 414 from moving with respect to the frame 402. In a particular embodiment the first superior locking collar 420 can be an end cap that can be integrally formed with the proximal end 416 of the superior spinous process support strap 414.

FIG. 4 and FIG. 5 show that a second superior locking collar 422 can be inserted over the distal end 418 of the superior spinous process support strap 414. Further, the second superior locking collar 422 can be slid over the superior spinous process support strap 414 until the second superior locking collar 422 is adjacent to the frame 402. Thereafter, the distal end 418 of the superior spinous process support strap 414 can be pulled through second superior locking collar 422 in order to tighten the superior spinous process strap 414 with respect to the frame 402. As described in detail below, the second superior locking collar 422 can engage the superior spinous process support strap 414 in order to prevent the second superior locking collar 422 from being removed from the superior spinous process support strap 414.

As shown in FIG. 4 and FIG. 5, a superior spinous process engagement structure 424 can extend from the superior portion 404 of the frame 402 toward a center of the frame 402. As described in detail below, the superior spinous process engagement structure 424 can engage a superior spinous process and prevent the superior portion 404 of the frame 402 from migrating with respect to the superior spinous process.

As illustrated in FIG. 4 and FIG. 5, the inferior portion 406 of the frame 402 can include a first hole 450 and a second hole 452. An inferior spinous process support strap 454 can be inserted through the first hole 450 and the second hole 452 and can span the inferior portion 406 of the frame 402. The inferior spinous process support strap 454 can include a proximal end 456 and a distal end 458. A first inferior locking collar 460 can engage the proximal end 456 of the inferior spinous process support strap 454 and prevent the proximal end 456 of the inferior spinous process support strap 454 from moving with respect to the frame 402. In a particular embodiment the first inferior locking collar 460 can be an end cap that can be integrally formed with the proximal end 456 of the inferior spinous process support strap 454.

FIG. 4 and FIG. 5 show that a second inferior locking collar 462 can be inserted over the distal end 458 of the inferior spinous process support strap 454. Further, the second inferior locking collar 462 can be slid over the inferior spinous process support strap 454 until the second inferior locking collar 462 is adjacent to the frame 402. Thereafter, the distal end 458 of the inferior spinous process support strap 454 can be pulled through second inferior locking collar 462 in order to tighten the inferior spinous process strap 454 with respect to the frame 402. As described in detail below, the second inferior locking collar 462 can engage the inferior spinous process support strap 454 in order to prevent the second inferior locking collar 462 from being removed from the inferior spinous process support strap 454.

As shown in FIG. 4 and FIG. 5, an inferior spinous process engagement structure 464 can extend from the inferior portion 406 of the frame 402 toward a center of the frame 402. As described in detail below, the inferior spinous process engagement structure 464 can engage an inferior spinous process and prevent the inferior portion 406 of the frame 402 from migrating with respect to the inferior spinous process.

In a particular embodiment, when the interspinous process brace 400 is properly installed between a superior vertebra and an inferior vertebra, the superior spinous process support strap 414 can engage and support a superior spinous process 500. Further, the inferior spinous process support strap 454 can engage and support an inferior spinous process 502. More specifically, the superior spinous process engagement structure 424 can extend slightly into and engage the superior spinous process 500. Also, the inferior spinous process engagement structure 464 can extend slightly into and engage the inferior spinous process 502. Accordingly, the spinous process engagement structures 424, 464 can substantially prevent the interspinous process brace 400 from migrating with respect to the spinous processes 500, 502.

Also, in a particular embodiment, the adjustable interspinous process brace 400 can be movable between a relaxed configuration, shown in FIG. 4, and a taut configuration, shown in FIG. 5. In the relaxed configuration, a distance 510 between the superior spinous process 500 and the inferior spinous process 502 can be at a minimum. However, as the spinous process support straps 414, 454 are tightened, as described herein, the distance 510 between the superior spinous process 500 and the inferior spinous process 502 can increase. Further, in the taut configuration each spinous process support strap 414, 454 can bind a spinous process 500, 502 between the spinous process support strap 414, 454 and the frame 402.

Accordingly, the interspinous process brace 400 can be installed between a superior spinous process 500 and an inferior spinous process 502. Further, the spinous support straps 414, 454 can be moved relative to the frame 402, e.g., by tightening the spinous support straps 414, 454 with respect to the frame 402, in order to increase the distance between the superior spinous process 500 and the inferior spinous process 502.

Alternatively, a distractor can be used to increase the distance between the superior spinous process 500 and the inferior spinous process 502 and the interspinous process brace 400 can be configured to support the superior spinous process 502 and the inferior spinous process 500. After the interspinous process brace 400 is configured accordingly, the distractor can be removed and the interspinous process brace 400 can support the superior spinous process 500 and the inferior spinous process 502 and substantially prevent the distance between the superior spinous process 500 and the inferior spinous process 502 from returning to a pre-distraction value.

Figure 6:
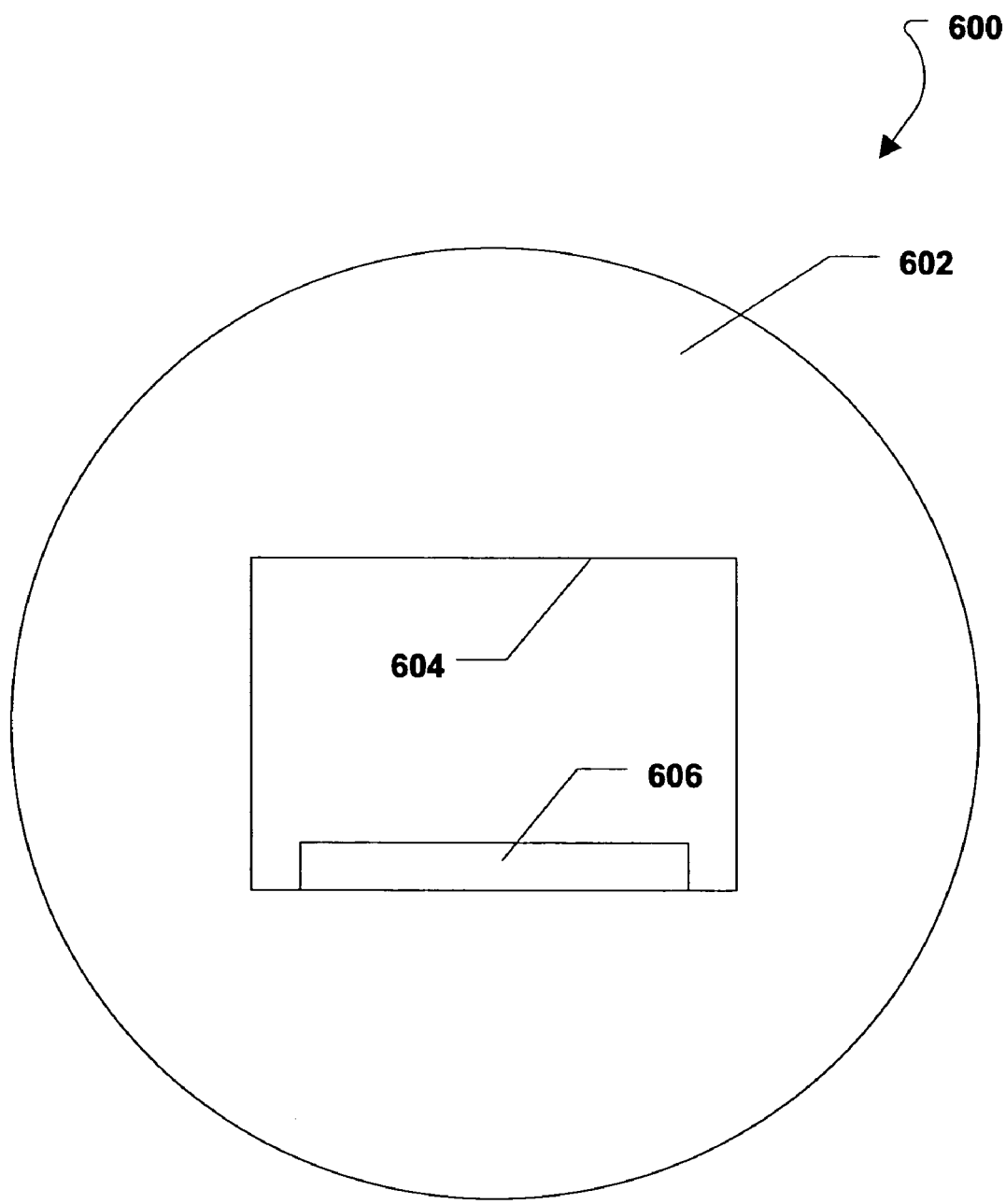
FIG. 6 is a plan view of a locking device.
Figure 7:
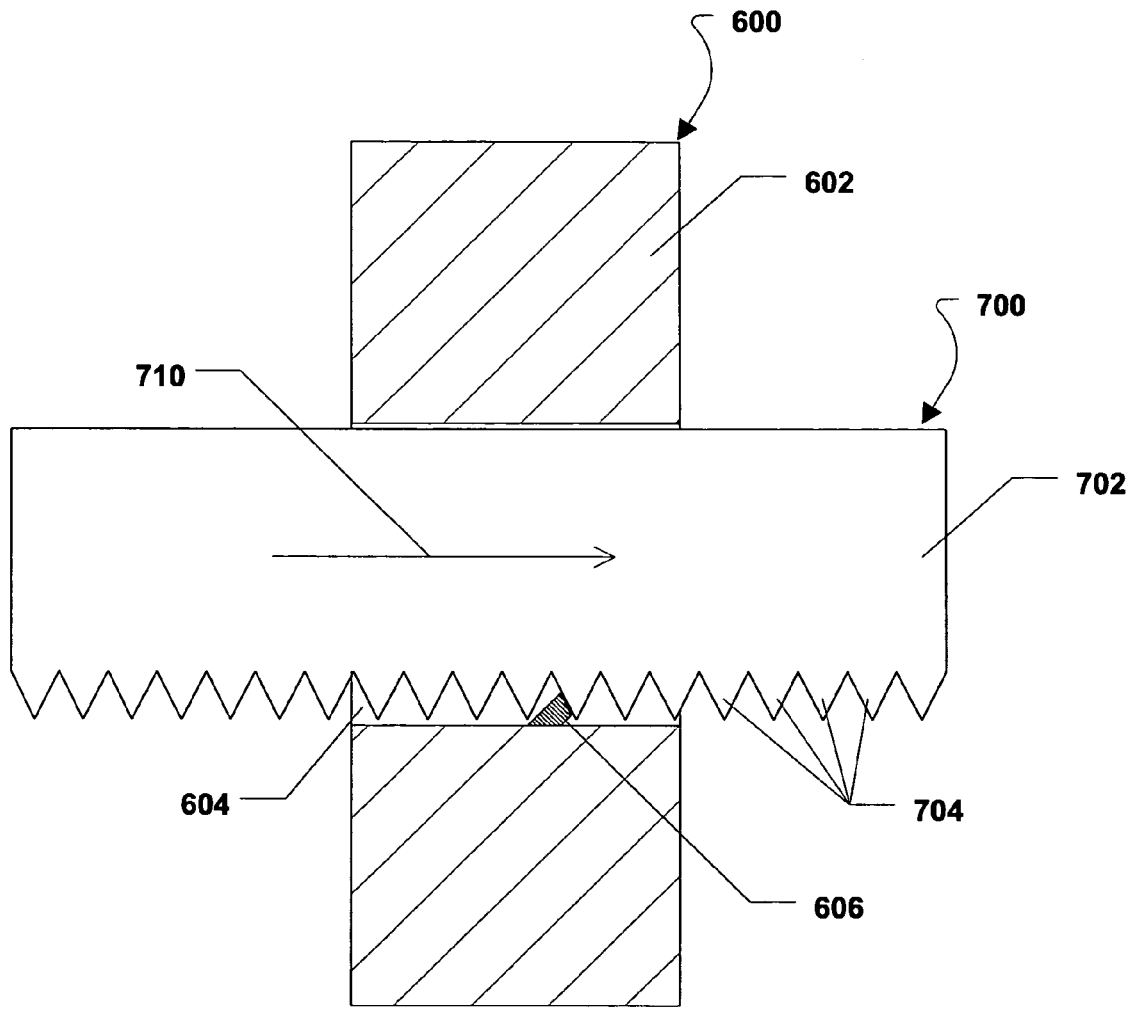
FIG. 7 is a cross-section view of the locking device with a spinous process support strap inserted therein.

FIG. 6 and FIG. 7 illustrates an embodiment of a locking collar generally designated 600. In a particular embodiment, one or more of the locking collars described herein can be substantially similar to the locking collar 600 shown in FIG. 6. As depicted, the locking collar 600 can include a body 602 formed with a central opening 604. Moreover, a pawl 606 can extend at least partially into the central opening 604 of the body 602.

FIG. 7 shows that a spinous process support strap 700 can be inserted through the central opening 604 of the body 602. In a particular embodiment, the spinous process support strap 700 can be one of the spinous process support straps described herein. As shown, the spinous process support strap 700 can include a body 702 having one or more teeth 704 formed therein.

In a particular embodiment, the pawl 606 can be hinged and elastic, and as the spinous process support strap 700 is inserted through the locking collar 600, in the direction indicated by the arrow 710, the teeth 704 of the spinous process support strap 700 can push the pawl 606 downward into the body 602 of the locking collar 600. However, in between adjacent teeth 704, the pawl 606 can return to a tooth engagement position and in which the pawl 606 extends into the area between adjacent teeth 704. In the tooth engagement position, the pawl 606 can engage a tooth 704 and prevent the spinous process support strap 700 from moving in a direction opposite the arrow 710.

Accordingly, as described above, a spinous process support strap can be inserted through a frame and looped at least partially around a spinous process. Further, the spinous process support strap can be tightened around the spinous process until the spinous process is cradled between the spinous process support strap and the frame.

Description of a Second Embodiment of an Interspinous Process Brace

Figure 8:
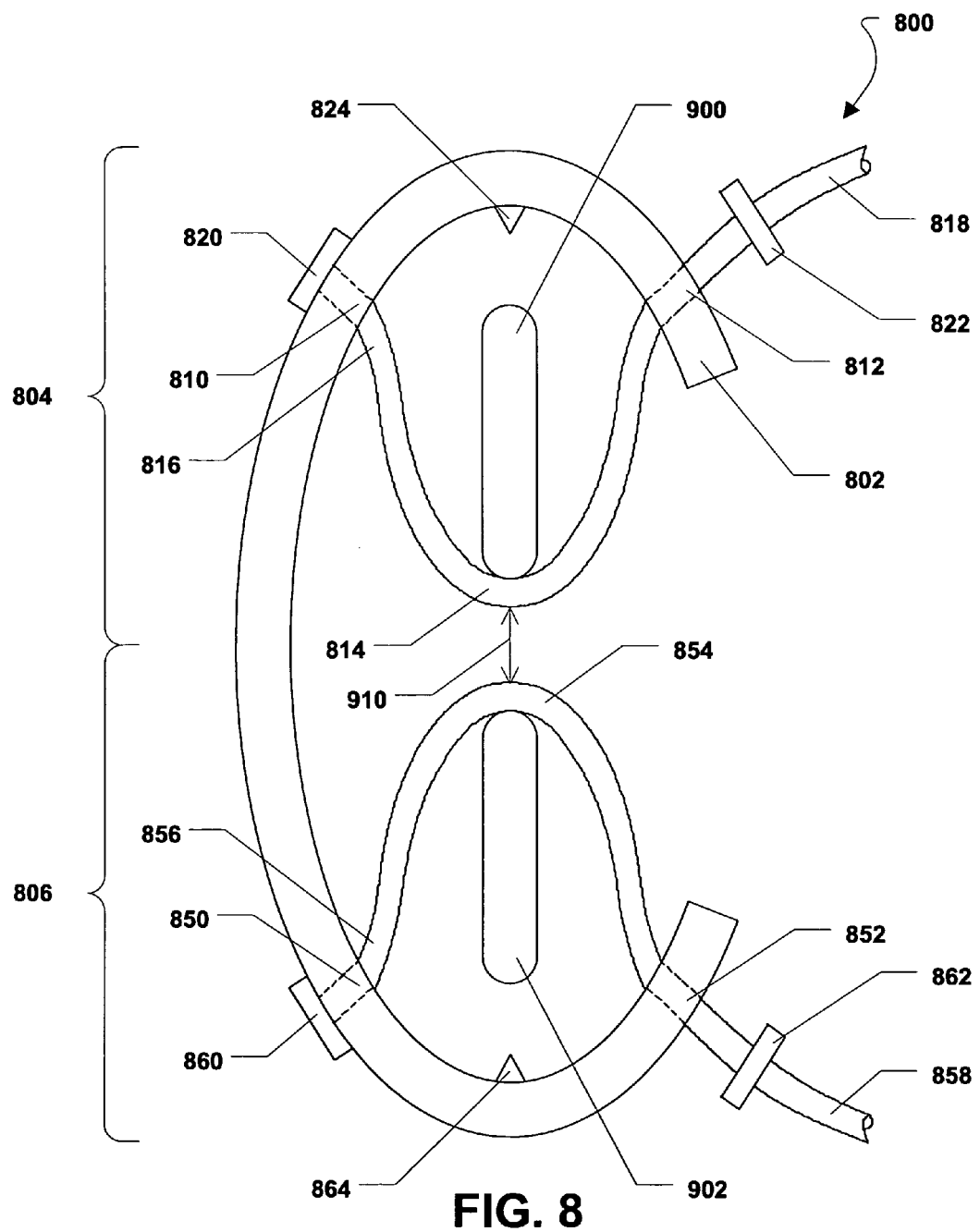
FIG. 8 is a plan view of a second interspinous process brace in a relaxed configuration.
Figure 9:
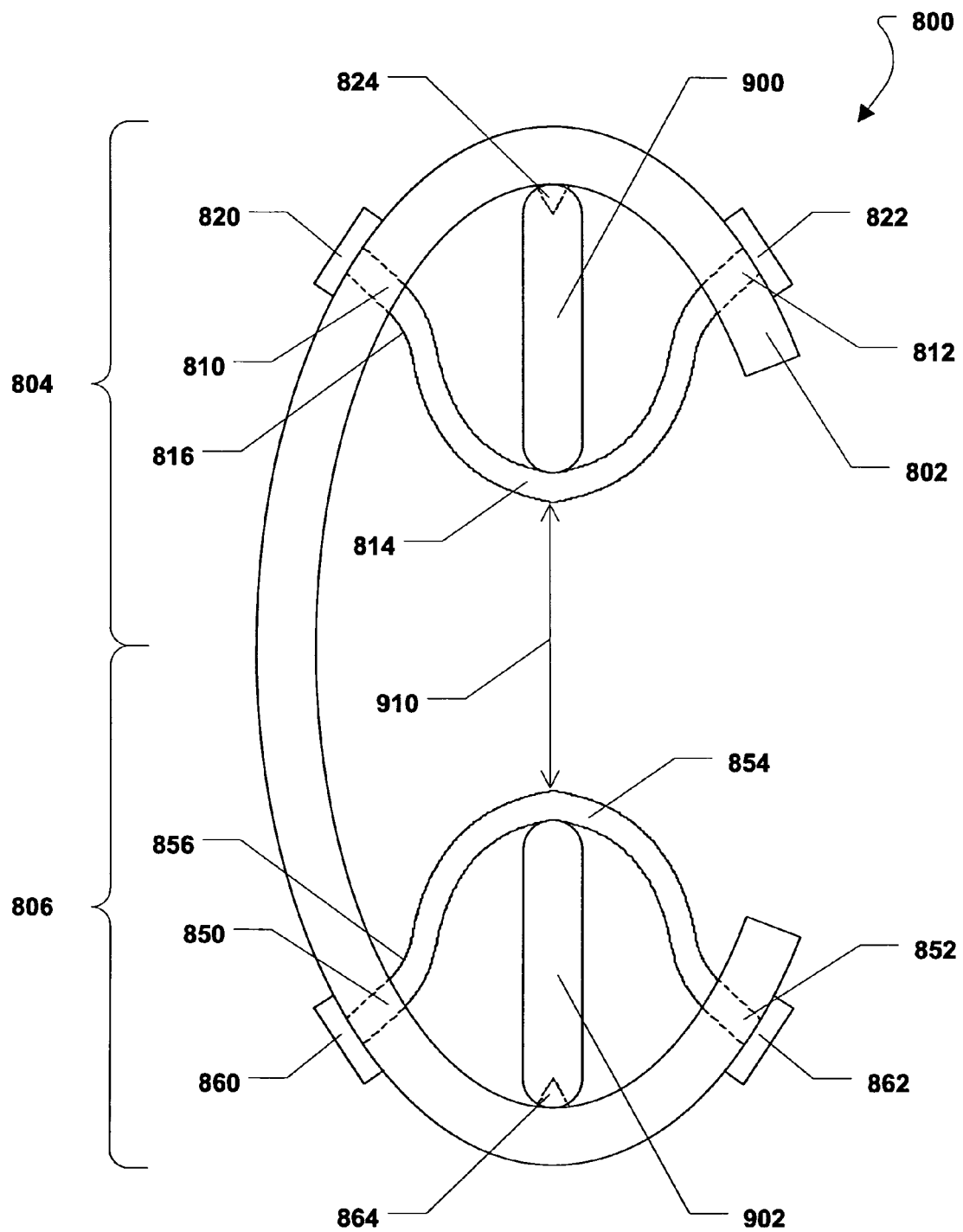
FIG. 9 is a plan view of the second interspinous process brace in a taut configuration.

Referring to FIG. 8 and FIG. 9, a second interspinous process brace is shown and is generally designated 800. As shown, the adjustable interspinous process brace 800 can include a generally C-shaped frame 802 that can include a superior portion 804 and an inferior portion 806. In a particular embodiment, the frame 802 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the frame 802 can be made from any other substantially rigid biocompatible materials.

As illustrated in FIG. 8 and FIG. 9, the superior portion 804 of the frame 802 can include a first hole 810 and a second hole 812. A superior spinous process support strap 814 can be inserted through the first hole 810 and the second hole 812 and can span the superior portion 804 of the frame 802. The superior spinous process support strap 814 can include a proximal end 816 and a distal end 818. A first superior locking collar 820 can engage the proximal end 816 of the superior spinous process support strap 814 and prevent the proximal end 816 of the superior spinous process support strap 814 from moving with respect to the frame 802. In a particular embodiment the first superior locking collar 820 can be an end cap that can be integrally formed with the proximal end 816 of the superior spinous process support strap 814.

FIG. 8 and FIG. 9 show that a second superior locking collar 822 can be inserted over the distal end 818 of the superior spinous process support strap 814. Further, the second superior locking collar 822 can be slid over the superior spinous process support strap 814 until the second superior locking collar 822 is adjacent to the frame 802. Thereafter, the distal end 818 of the superior spinous process support strap 814 can be pulled through second superior locking collar 822 in order to tighten the superior spinous process strap 814 with respect to the frame 802. As described in detail below, the second superior locking collar 822 can engage the superior spinous process support strap 814 in order to prevent the second superior locking collar 822 from being removed from the superior spinous process support strap 814.

As shown in FIG. 8 and FIG. 9, a superior spinous process engagement structure 824 can extend from the superior portion 804 of the frame 802 toward a center of the frame 802. As described in detail below, the superior spinous process engagement structure 824 can engage a superior spinous process and prevent the superior portion 804 of the frame 802 from migrating with respect to the superior spinous process.

As illustrated in FIG. 8 and FIG. 9, the inferior portion 806 of the frame 802 can include a first hole 850 and a second hole 852. An inferior spinous process support strap 854 can be inserted through the first hole 850 and the second hole 852 and can span the inferior portion 806 of the frame 802. The inferior spinous process support strap 854 can include a proximal end 856 and a distal end 858. A first inferior locking collar 860 can engage the proximal end 856 of the inferior spinous process support strap 854 and prevent the proximal end 856 of the inferior spinous process support strap 854 from moving with respect to the frame 802. In a particular embodiment the first inferior locking collar 860 can be an end cap that can be integrally formed with the proximal end 856 of the inferior spinous process support strap 854.

FIG. 8 and FIG. 9 show that a second inferior locking collar 862 can be inserted over the distal end 858 of the inferior spinous process support strap 854. Further, the second inferior locking collar 862 can be slid over the inferior spinous process support strap 854 until the second inferior locking collar 862 is adjacent to the frame 802. Thereafter, the distal end 858 of the inferior spinous process support strap 854 can be pulled through second inferior locking collar 862 in order to tighten the inferior spinous process strap 854 with respect to the frame 802. As described in detail below, the second inferior locking collar 862 can engage the inferior spinous process support strap 854 in order to prevent the second inferior locking collar 862 from being removed from the inferior spinous process support strap 854.

As shown in FIG. 8 and FIG. 9, an inferior spinous process engagement structure 864 can extend from the inferior portion 806 of the frame 802 toward a center of the frame 802. As described in detail below, the inferior spinous process engagement structure 864 can engage an inferior spinous process and prevent the inferior portion 806 of the frame 802 from migrating with respect to the inferior spinous process.

In a particular embodiment, when the interspinous process brace 800 is properly installed between a superior vertebra and an inferior vertebra, the superior spinous process support strap 814 can engage and support a superior spinous process 900. Further, the inferior spinous process support strap 854 can engage and support an inferior spinous process 902. More specifically, the superior spinous process engagement structure 824 can extend slightly into and engage the superior spinous process 900. Also, the inferior spinous process engagement structure 864 can extend slightly into and engage the inferior spinous process 902. Accordingly, the spinous process engagement structures 824, 864 can substantially prevent the interspinous process brace 800 from migrating with respect to the spinous processes 900, 902.

Also, in a particular embodiment, the adjustable interspinous process brace 800 can be movable between a relaxed configuration, shown in FIG. 8, and a taut configuration, shown in FIG. 9. In the relaxed configuration, a distance 910 between the superior spinous process 900 and the inferior spinous process 902 can be at a minimum. However, as the spinous process support straps 814, 854 are tightened, as described herein, the distance 910 between the superior spinous process 900 and the inferior spinous process 902 can increase. Further, in the taut configuration each spinous process support strap 814, 854 can bind a spinous process 900, 902 between the spinous process support strap 814, 854 and the frame 802.

Accordingly, the interspinous process brace 800 can be installed between a superior spinous process 900 and an inferior spinous process 902. Further, the spinous support straps 814, 854 can be moved relative to the frame 802, e.g., by tightening the spinous support straps 814, 854 with respect to the frame 802, in order to increase the distance between the superior spinous process 900 and the inferior spinous process 902.

Alternatively, a distractor can be used to increase the distance between the superior spinous process 900 and the inferior spinous process 902 and the interspinous process brace 800 can be configured to support the superior spinous process 902 and the inferior spinous process 900. After the interspinous process brace 800 is configured accordingly, the distractor can be removed and the interspinous process brace 800 can support the superior spinous process 900 and the inferior spinous process 902 and substantially prevent the distance between the superior spinous process 900 and the inferior spinous process 902 from returning to a pre-distraction value.

Description of a Third Embodiment of an Interspinous Process Brace

Figure 10:
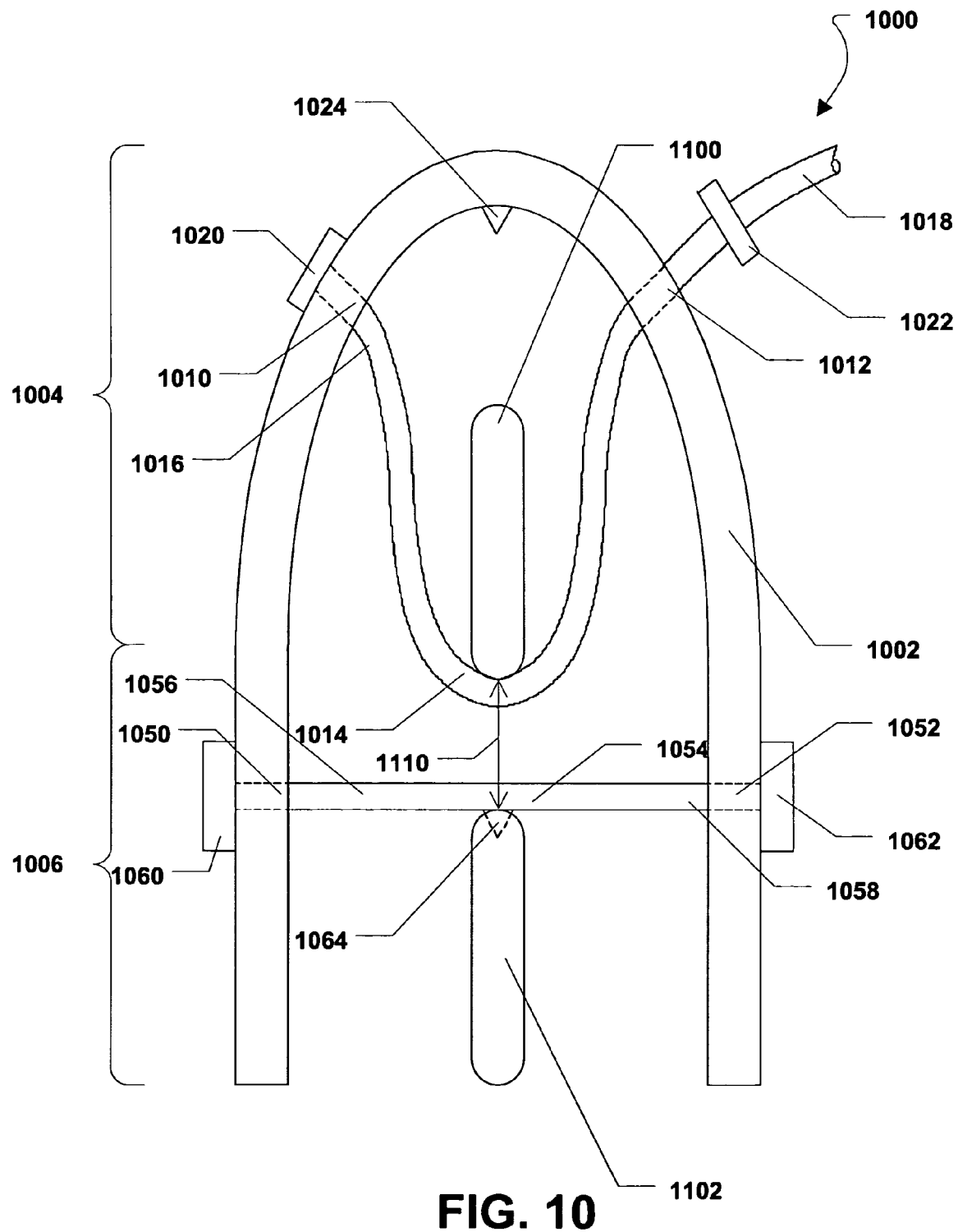
FIG. 10 is a plan view of a third interspinous process brace in a relaxed configuration.
Figure 11:
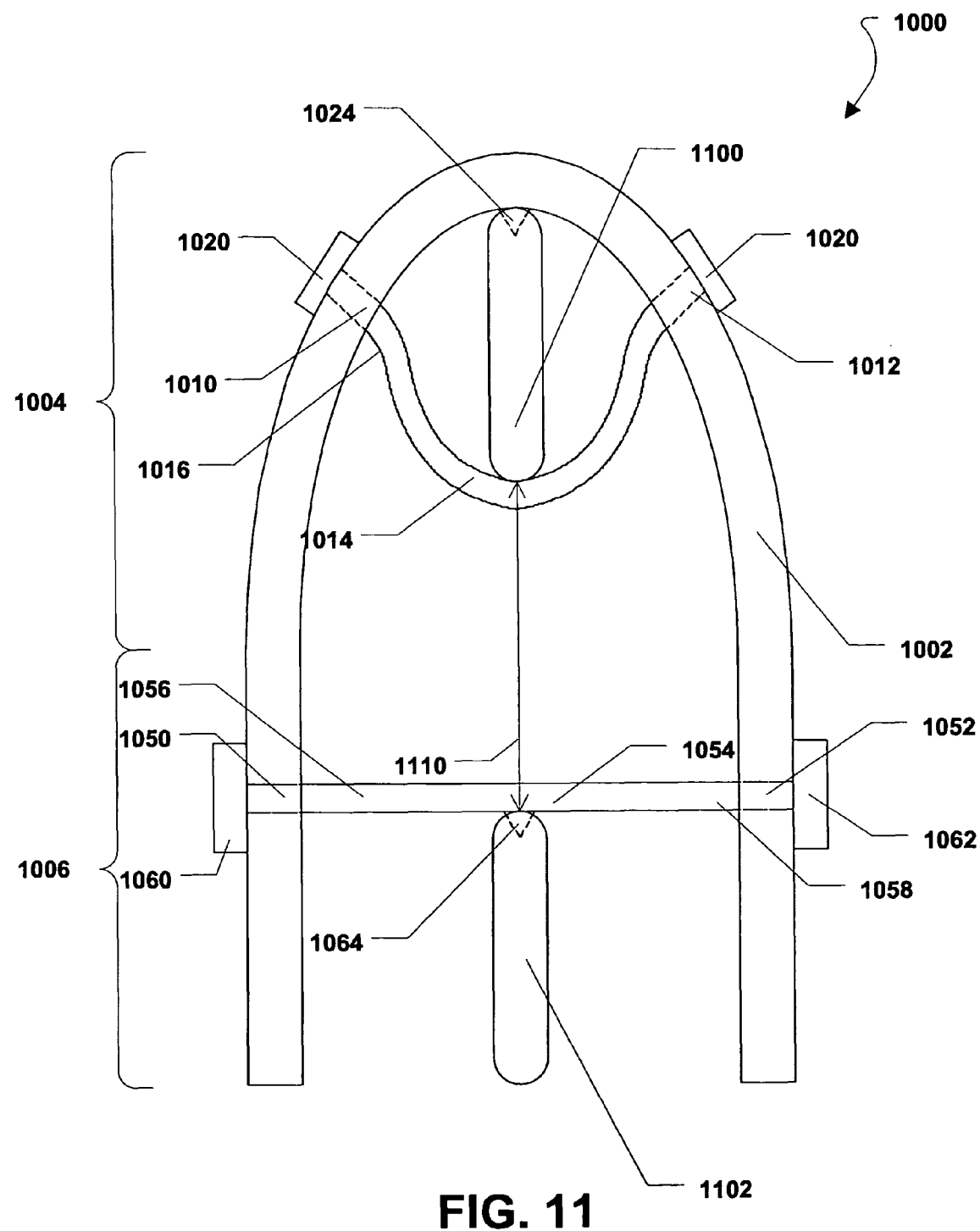
FIG. 11 is a plan view of the third interspinous process brace in a taut configuration.

Referring to FIG. 10 and FIG. 11, a third interspinous process brace is shown and is generally designated 1000. As shown, the adjustable interspinous process brace 1000 can include a generally U-shaped frame 1002 that can include a superior portion 1004 and an inferior portion 1006. In a particular embodiment, the frame 1002 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the frame 1002 can be made from any other substantially rigid biocompatible materials.

As illustrated in FIG. 10 and FIG. 11, the superior portion 1004 of the frame 1002 can include a first hole 1010 and a second hole 1012. A superior spinous process support strap 1014 can be inserted through the first hole 1010 and the second hole 1012 and can span the superior portion 1004 of the frame 1002. The superior spinous process support strap 1014 can include a proximal end 1016 and a distal end 1018. A first superior locking collar 1020 can engage the proximal end 1016 of the superior spinous process support strap 1014 and prevent the proximal end 1016 of the superior spinous process support strap 1014 from moving with respect to the frame 1002. In a particular embodiment the first superior locking collar 1020 can be an end cap that can be integrally formed with the proximal end 1016 of the superior spinous process support strap 1014.

FIG. 10 and FIG. 11 show that a second superior locking collar 1022 can be inserted over the distal end 1018 of the superior spinous process support strap 1014. Further, the second superior locking collar 1022 can be slid over the superior spinous process support strap 1014 until the second superior locking collar 1022 is adjacent to the frame 1002. Thereafter, the distal end 1018 of the superior spinous process support strap 1014 can be pulled through second superior locking collar 1022 in order to tighten the superior spinous process strap 1014 with respect to the frame 1002. As described in detail below, the second superior locking collar 1022 can engage the superior spinous process support strap 1014 in order to prevent the second superior locking collar 1022 from being removed from the superior spinous process support strap 1014.

As shown in FIG. 10 and FIG. 11, a superior spinous process engagement structure 1024 can extend from the superior portion 1004 of the frame 1002 toward a center of the frame 1002. As described in detail below, the superior spinous process engagement structure 1024 can engage a superior spinous process and prevent the superior portion 1004 of the frame 1002 from migrating with respect to the superior spinous process.

As illustrated in FIG. 10 and FIG. 11, the inferior portion 1006 of the frame 1002 can include a first hole 1050 and a second hole 1052. An inferior spinous process support bracket 1054 can be inserted through the first hole 1050 and the second hole 1052 and can span the superior portion 1006 of the frame 1002. The inferior spinous process support bracket 1054 can include a proximal end 1056 and a distal end 1058. A first inferior locking collar 1060 can engage the proximal end 1056 of the inferior spinous process support bracket 1054 and prevent the proximal end 1056 of the inferior spinous process support bracket 1054 from moving with respect to the frame 1002. In a particular embodiment the first inferior locking collar 1060 can be an end cap that can be integrally formed with the proximal end 1056 of the inferior spinous process support bracket 1054.

FIG. 10 and FIG. 11 show that a second inferior locking collar 1062 can be inserted over the distal end 1058 of the inferior spinous process support strap 1054. In a particular embodiment, the distal end 1058 of the inferior spinous support bracket 1054 can be threaded and the second inferior locking collar 1062 can also be threaded. As such, the second inferior locking collar 1062 can be threadably engaged with the inferior spinous process support bracket 1054 to prevent the inferior spinous process support bracket 1054 from moving with respect to the frame 1002.

As shown in FIG. 10 and FIG. 11, an inferior spinous process engagement structure 1064 can extend from the inferior spinous process support bracket 1054 toward a bottom of the frame 1002. As described in detail below, the inferior spinous process engagement structure 1064 can engage an inferior spinous process and prevent the inferior portion 1006 of the frame 1002 from migrating with respect to the inferior spinous process.

In a particular embodiment, when the interspinous process brace 1000 is properly installed between a superior vertebra and an inferior vertebra, the superior spinous process support strap 1014 can engage and support a superior spinous process 1100. Further, the inferior spinous process support bracket 1054 can engage and support an inferior spinous process 1102. More specifically, the superior spinous process engagement structure 1024 can extend slightly into and engage the superior spinous process 1100. Also, the inferior spinous process engagement structure 1064 can extend slightly into and engage the inferior spinous process 1102. Accordingly, the spinous process engagement structures 1024, 1064 can substantially prevent the interspinous process brace 1000 from migrating with respect to the spinous processes 1100, 1102.

Also, in a particular embodiment, the adjustable interspinous process brace 1000 can be movable between a relaxed configuration, shown in FIG. 10, and a taut configuration, shown in FIG. 11. In the relaxed configuration, a distance 1110 between the superior spinous process 1100 and the inferior spinous process 1102 can be at a minimum. However, as the superior spinous process support strap 1014 is tightened, as described herein, the distance 1110 between the superior spinous process 1100 and the inferior spinous process 1102 can increase. Further, in the taut configuration the superior spinous process support strap 1014 can bind the superior spinous process 1100 between the superior spinous process support strap 1014 and the frame 1002.

Accordingly, the interspinous process brace 1000 can be installed between a superior spinous process 1100 and an inferior spinous process 1102. Further, the superior spinous support strap 1014 can be moved relative to the frame 1002, e.g., by tightening the superior spinous support strap 1014 with respect to the frame 1002, in order to increase the distance between the superior spinous process 1100 and the inferior spinous process 1102.

Alternatively, a distractor can be used to increase the distance between the superior spinous process 1100 and the inferior spinous process 1102 and the interspinous process brace 1000 can be configured to support the superior spinous process 1102 and the inferior spinous process 1100. After the interspinous process brace 1000 is configured accordingly, the distractor can be removed and the interspinous process brace 1000 can support the superior spinous process 1100 and the inferior spinous process 1102 and substantially prevent the distance between the superior spinous process 1100 and the inferior spinous process 1102 from returning to a pre-distraction value.

Description of a Fourth Embodiment of an Interspinous Process Brace

Figure 12:
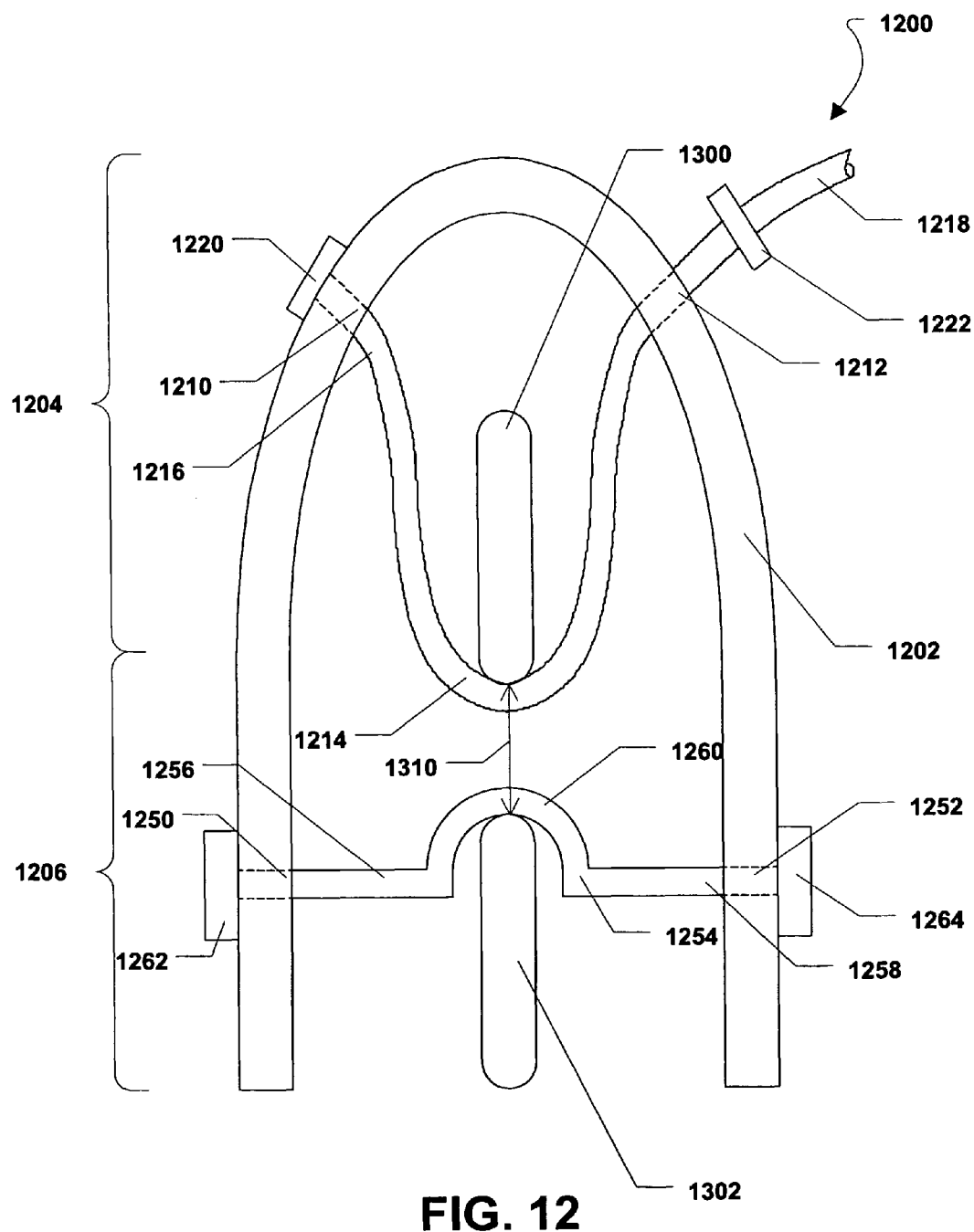
FIG. 12 is a plan view of a fourth interspinous process brace in a relaxed configuration.
Figure 13:
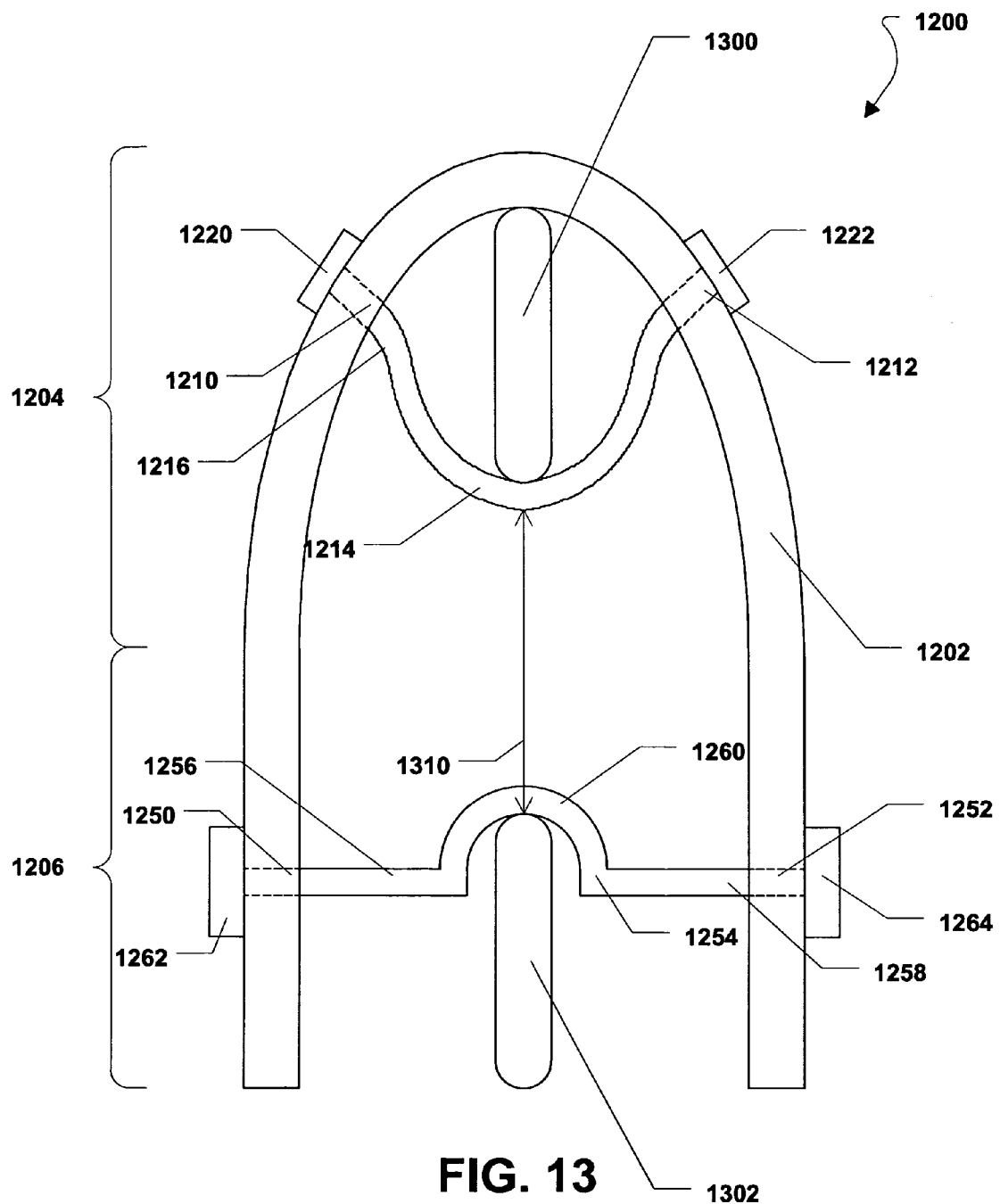
FIG. 13 is a plan view of the fourth interspinous process brace in a taut configuration.

Referring to FIG. 12 and FIG. 13, a fourth interspinous process brace is shown and is generally designated 1200. As shown, the adjustable interspinous process brace 1200 can include a generally U-shaped frame 1202 that can include a superior portion 1204 and an inferior portion 1206. In a particular embodiment, the frame 1202 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the frame 1202 can be made from any other substantially rigid biocompatible materials.

As illustrated in FIG. 12 and FIG. 13, the superior portion 1204 of the frame 1202 can include a first hole 1210 and a second hole 1212. A superior spinous process support strap 1214 can be inserted through the first hole 1210 and the second hole 1212 and can span the superior portion 1204 of the frame 1202. The superior spinous process support strap 1214 can include a proximal end 1216 and a distal end 1218. A first superior locking collar 1220 can engage the proximal end 1216 of the superior spinous process support strap 1214 and prevent the proximal end 1216 of the superior spinous process support strap 1214 from moving with respect to the frame 1202. In a particular embodiment the first superior locking collar 1220 can be an end cap that can be integrally formed with the proximal end 1216 of the superior spinous process support strap 1214.

FIG. 12 and FIG. 13 show that a second superior locking collar 1222 can be inserted over the distal end 1218 of the superior spinous process support strap 1214. Further, the second superior locking collar 1222 can be slid over the superior spinous process support strap 1214 until the second superior locking collar 1222 is adjacent to the frame 1202. Thereafter, the distal end 1218 of the superior spinous process support strap 1214 can be pulled through second superior locking collar 1222 in order to tighten the superior spinous process strap 1214 with respect to the frame 1202. As described in detail below, the second superior locking collar 1222 can engage the superior spinous process support strap 1214 in order to prevent the second superior locking collar 1222 from being removed from the superior spinous process support strap 1214.

As illustrated in FIG. 12 and FIG. 13, the inferior portion 1206 of the frame 1202 can include a first hole 1250 and a second hole 1252. An inferior spinous process support bracket 1254 can be inserted through the first hole 1250 and the second hole 1252 and can span the inferior portion 1204 of the frame 1202. The inferior spinous process support bracket 1254 can include a proximal end 1256 and a distal end 1258. Further, the inferior spinous process support bracket 1254 can include a curved central portion 1260 that is configured to receive a spinous process.

FIG. 12 and FIG. 13 indicate that a first inferior locking collar 1262 can engage the proximal end 1256 of the inferior spinous process support bracket 1254 and prevent the proximal end 1256 of the inferior spinous process support bracket 1254 from moving with respect to the frame 1202. Further, a second inferior locking collar 1264 can engage the distal end 1258 of the inferior spinous process support strap 1254. In a particular embodiment, the proximal end 1256 and the distal end 1258 of the inferior spinous support bracket 1254 can be threaded. Also, the first inferior locking collar 1262 and the second inferior locking collar 1264 can be threaded. As such, the inferior locking collars 1262, 1264 can be threadably engaged with the inferior spinous process support bracket 1254 to prevent the inferior spinous process support bracket 1254 from moving with respect to the frame 1202.

In a particular embodiment, when the interspinous process brace 1200 is properly installed between a superior vertebra and an inferior vertebra, the superior spinous process support strap 1214 can engage and support a superior spinous process 1300. Further, the inferior spinous process support bracket 1254 can engage and support an inferior spinous process 1302.

Also, in a particular embodiment, the adjustable interspinous process brace 1200 can be movable between a relaxed configuration, shown in FIG. 12, and a taut configuration, shown in FIG. 13. In the relaxed configuration, a distance 1310 between the superior spinous process 1300 and the inferior spinous process 1302 can be at a minimum. However, as the superior spinous process support strap 1214 is tightened, as described herein, the distance 1310 between the superior spinous process 1300 and the inferior spinous process 1302 can increase. Further, in the taut configuration the superior spinous process support strap 1214 can bind the superior spinous process 1300 between the superior spinous process support strap 1214 and the frame 1202.

Accordingly, the interspinous process brace 1200 can be installed between a superior spinous process 1300 and an inferior spinous process 1302. Further, the superior spinous support strap 1214 can be moved relative to the frame 1202, e.g., by tightening the superior spinous support strap 1214 with respect to the frame 1202, in order to increase the distance between the superior spinous process 1300 and the inferior spinous process 1302.

Alternatively, a distractor can be used to increase the distance between the superior spinous process 1300 and the inferior spinous process 1302 and the interspinous process brace 1200 can be configured to support the superior spinous process 1302 and the inferior spinous process 1300. After the interspinous process brace 1200 is configured accordingly, the distractor can be removed and the interspinous process brace 1200 can support the superior spinous process 1300 and the inferior spinous process 1302 and substantially prevent the distance between the superior spinous process 1300 and the inferior spinous process 1302 from returning to a pre-distraction value.

Description of a Fifth Embodiment of an Interspinous Process Brace

Figure 14:
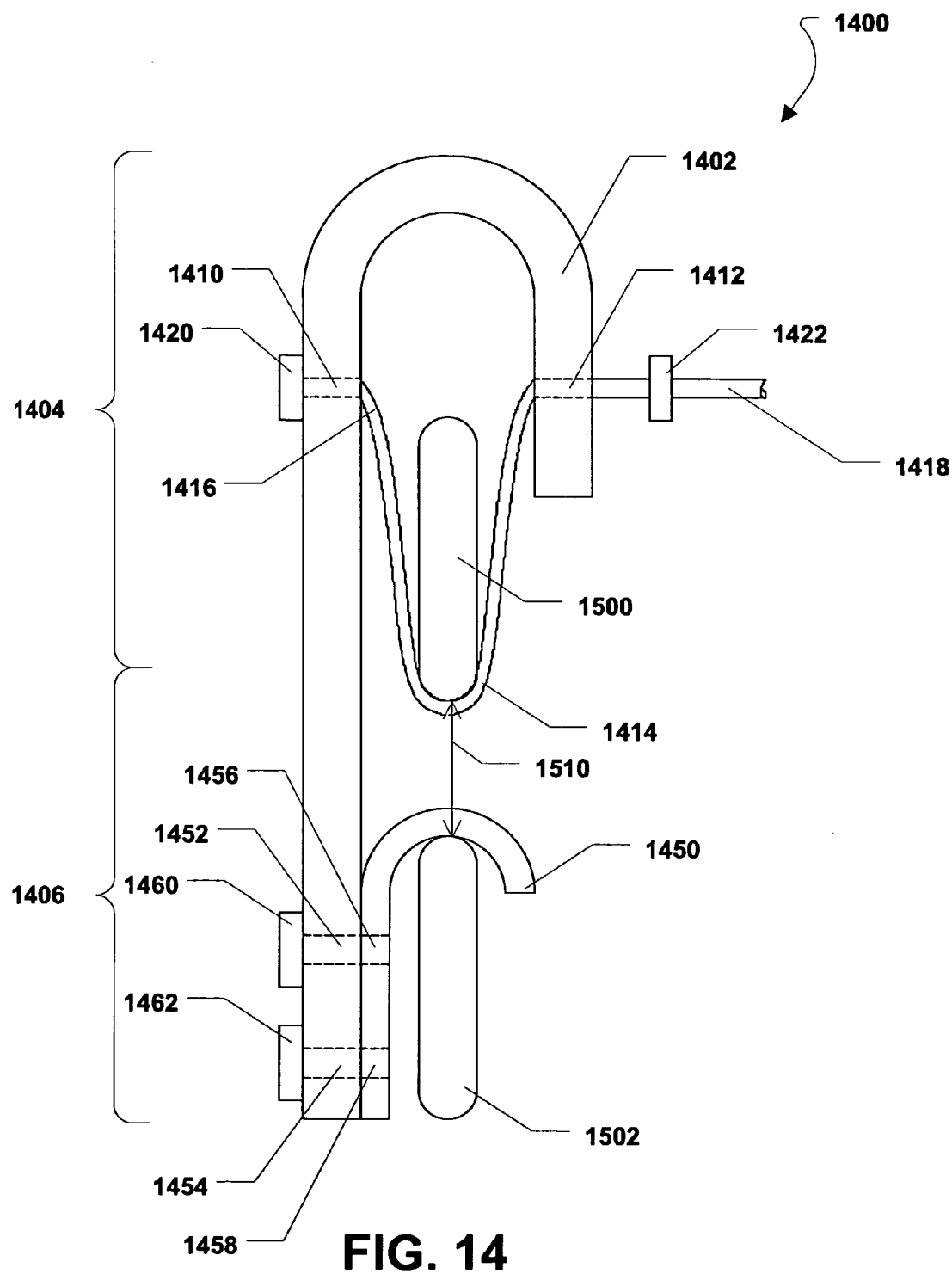
FIG. 14 is a plan view of a fifth interspinous process brace in a relaxed configuration.
Figure 15:
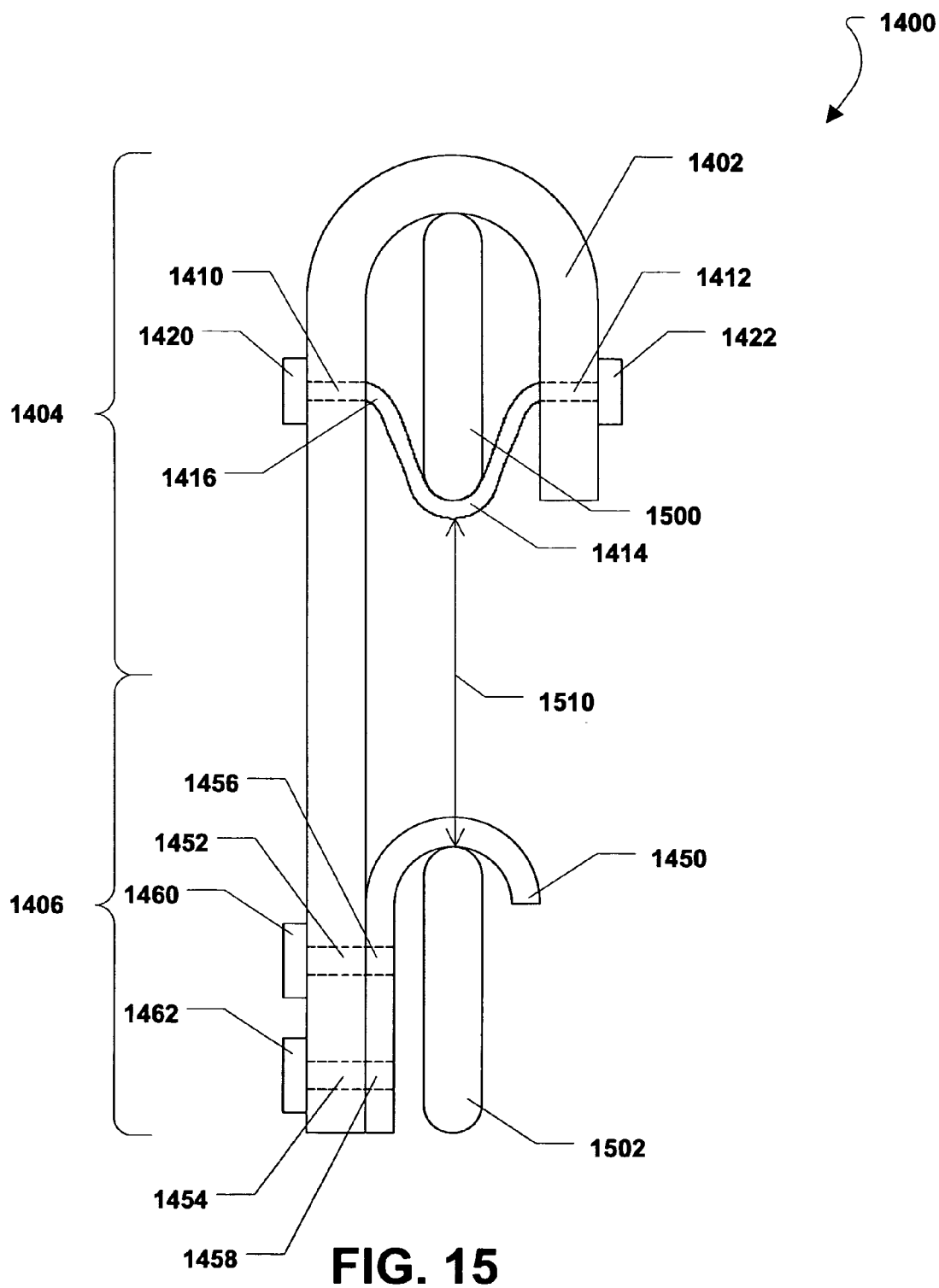
FIG. 15 is a plan view of the fifth interspinous process brace in a taut configuration.

Referring to FIG. 14 and FIG. 15, a fifth interspinous process brace is shown and is generally designated 1400. As shown, the adjustable interspinous process brace 1400 can include a generally J-shaped frame 1402 that can include a superior portion 1404 and an inferior portion 1406. In a particular embodiment, the frame 1402 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the frame 1402 can be made from any other substantially rigid biocompatible materials.

As illustrated in FIG. 14 and FIG. 15, the superior portion 1404 of the frame 1402 can include a first hole 1410 and a second hole 1412. A superior spinous process support strap 1414 can be inserted through the first hole 1410 and the second hole 1412 and can span the superior portion 1404 of the frame 1402. The superior spinous process support strap 1414 can include a proximal end 1416 and a distal end 1418. A first superior locking collar 1420 can engage the proximal end 1416 of the superior spinous process support strap 1414 and prevent the proximal end 1416 of the superior spinous process support strap 1414 from moving with respect to the frame 1402. In a particular embodiment the first superior locking collar 1420 can be an end cap that can be integrally formed with the proximal end 1416 of the superior spinous process support strap 1414.

FIG. 14 and FIG. 15 show that a second superior locking collar 1422 can be inserted over the distal end 1418 of the superior spinous process support strap 1414. Further, the second superior locking collar 1422 can be slid over the superior spinous process support strap 1414 until the second superior locking collar 1422 is adjacent to the frame 1402. Thereafter, the distal end 1418 of the superior spinous process support strap 1414 can be pulled through second superior locking collar 1422 in order to tighten the superior spinous process strap 1414 with respect to the frame 1402. As described in detail below, the second superior locking collar 1422 can engage the superior spinous process support strap 1414 in order to prevent the second superior locking collar 1422 from being removed from the superior spinous process support strap 1414.

As illustrated in FIG. 14 and FIG. 15, the inferior portion 1406 of the frame 1402 can include an inferior spinous process support bracket 1450 attached thereto. The inferior portion 1406 of the frame 1402 can include a first hole 1452 and a second hole 1454. Further, the inferior spinous process support bracket 1450 can include a first hole 1456 and a second hole 1458. In a particular embodiment, the holes 456, 1458 in the inferior spinous support bracket 1450 can be threaded. A first threaded fastener 1460 can be installed through the first hole 1452 in the inferior portion 1406 of the frame 1402 and can be threadably engaged with the first hole 1456 in the inferior spinous process support bracket 1450. Also, a second threaded fastener 1462 can be installed through the second hole 1454 in the inferior portion 1406 of the frame 1402 and can be threadably engaged with the second hole 1458 in the inferior spinous process support bracket 1450.

In a particular embodiment, when the interspinous process brace 1400 is properly installed between a superior vertebra and an inferior vertebra, the superior spinous process support strap 1414 can engage and support a superior spinous process 1500. Further, the inferior spinous process support bracket 1450 can engage and support an inferior spinous process 1502.

Also, in a particular embodiment, the adjustable interspinous process brace 1400 can be movable between a relaxed configuration, shown in FIG. 14, and a taut configuration, shown in FIG. 15. In the relaxed configuration, a distance 1510 between the superior spinous process 1500 and the inferior spinous process 1502 can be at a minimum. However, as the superior spinous process support strap 1414 is tightened, as described herein, the distance 1510 between the superior spinous process 1500 and the inferior spinous process 1502 can increase. Further, in the taut configuration the superior spinous process support strap 1414 can bind the superior spinous process 1500 between the superior spinous process support strap 1414 and the frame 1402.

Accordingly, the interspinous process brace 1400 can be installed between a superior spinous process 1500 and an inferior spinous process 1502. Further, the superior spinous support strap 1414 can be moved relative to the frame 1402, e.g., by tightening the superior spinous support strap 1414 with respect to the frame 1402, in order to increase the distance between the superior spinous process 1500 and the inferior spinous process 1502.

Alternatively, a distractor can be used to increase the distance between the superior spinous process 1500 and the inferior spinous process 1502 and the interspinous process brace 1400 can be configured to support the superior spinous process 1502 and the inferior spinous process 1500. After the interspinous process brace 1400 is configured accordingly, the distractor can be removed and the interspinous process brace 1400 can support the superior spinous process 1500 and the inferior spinous process 1502 and substantially prevent the distance between the superior spinous process 1500 and the inferior spinous process 1502 from returning to a pre-distraction value.

Description of a Method of Treating a Spine

Figure 16:
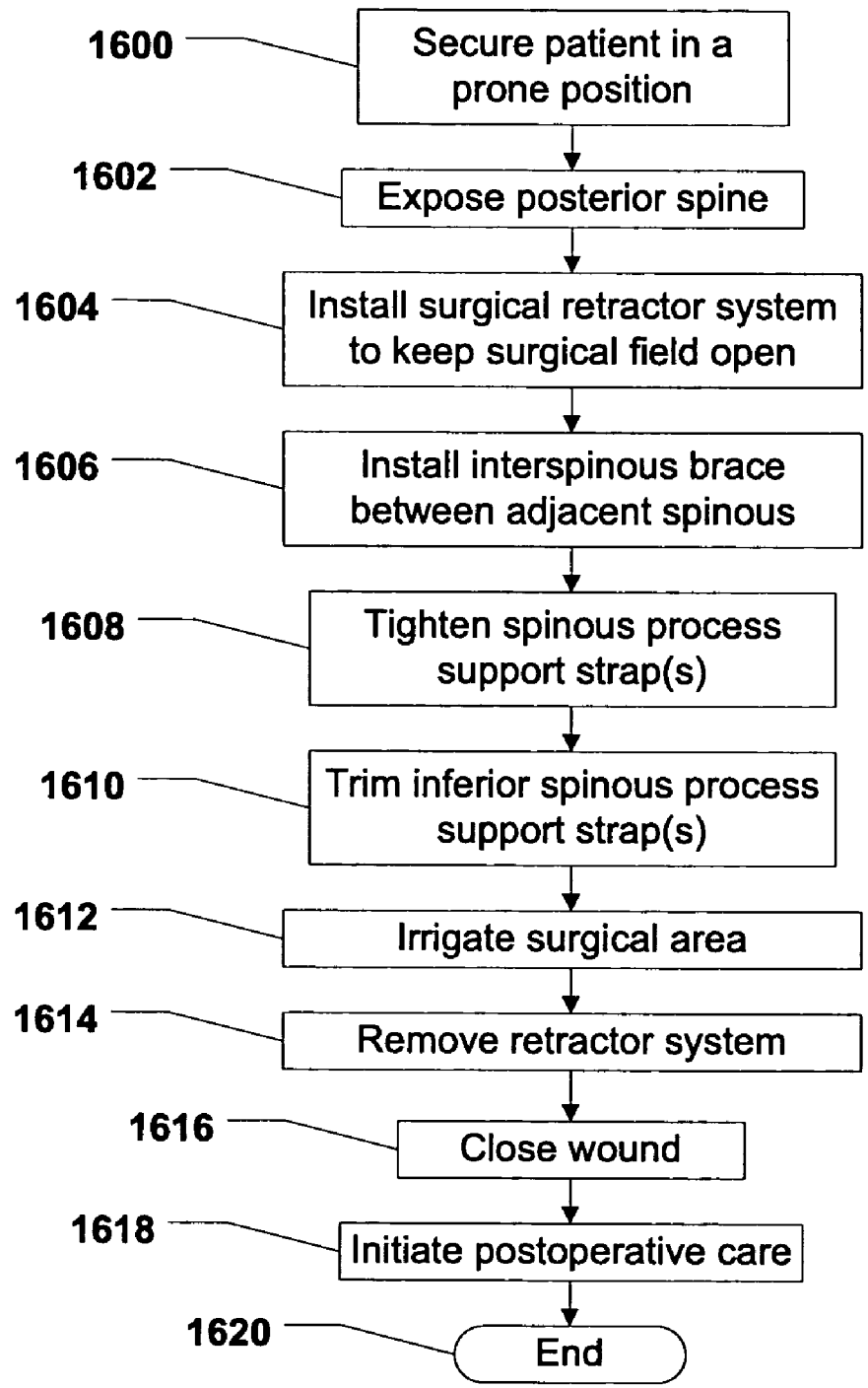
FIG. 16 is a flow chart illustrating a method of treating a spine.

Referring to FIG. 16, a method of treating a spine is shown and commences at block 1600. At block 1600, a patient can be secured in a prone position, e.g., on an operating table. At block 1602, the posterior spine can be exposed in order to expose adjacent spinous processes. Further, at block 1604, a surgical retractor system can be installed to keep surgical field open.

Moving to block 1606, a spinous process brace can be installed between two adjacent spinous processes. In a particular embodiment, the spinous process brace can be a spinous process brace according to one or more embodiments described herein. At block 1608, one or more spinous process support straps can be tightened. For example, each spinous process support strap can be tightened around a corresponding spinous process. At block 1610, the one or more spinous process support straps can be trimmed to remove any excess material. For example, after each spinous support strap is tightened as described herein, an end of the spinous support strap may be dangling from the spinous process brace. In order to prevent damage to surrounding tissue, the end of the spinous process support strap can be trimmed as described.

Continuing to block 1612, the surgical area can be irrigated. At block 1614, the retractor system can be removed. Further, at block 1616, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 1618, postoperative care can be initiated. The method can end at state 1620.

CONCLUSION

With the configuration of structure described above, the adjustable interspinous process brace provides a device that can be used to treat a spine and substantially alleviate or minimize one or more symptoms associated with disc degeneration, facet joint degeneration, or a combination thereof. For example, the adjustable interspinous process brace can installed between adjacent spinous processes in order to support the spinous processes and maintain them at or near a predetermined distance there between.

Although exemplary embodiments of the brace have been referred to as "interspinous process brace", such reference is for illustrative convenience and is not intended to be limiting in any capacity. For example, the brace can also find utility as an intervertebral process brace supporting two or more other vertebral processes (e.g., transverse processes or articular processes) or in other applications where separation or relative spatial support is desired between two or more hard tissue bodies.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An intervertebral process brace, comprising:
    a frame configured to support an upper vertebral process and a lower vertebral process, wherein the frame has:
        an inwardly facing upper concave surface configured to extend around a superior surface of the upper vertebral process;
        an opposing inwardly facing lower concave surface configured to extend around an inferior surface of the lower vertebral process;
        an outwardly facing upper convex surface corresponding to the upper concave surface;
        an outwardly facing lower convex surface corresponding to the lower concave surface;
        the upper concave surface and the upper convex surface each having respective maximum points;
        the lower concave surface and the lower convex surface each having respective minimum points;
        the inwardly facing upper and lower concave surfaces and the outwardly facing upper and lower convex surfaces being integrally formed portions of the frame;
    a first flexible vertebral process support strap spanning a first portion of the frame, wherein the first vertebral process support strap is configured to engage an inferior surface of the upper vertebral process and bind the upper vertebral process between the first vertebral process support strap and the first portion of the frame;
    a locking collar attached on the first vertebral process support strap; the locking collar being simultaneously movable relative to the frame and slidable along the first vertebral process support strap; the locking collar operative to secure the first vertebral process support strap to the frame;
    wherein when the intervertebral process brace is disposed such that the frame supports the upper and lower vertebral processes and the first strap engages an inferior surface of the upper vertebral process, the inwardly facing upper and lower concave surfaces and the outwardly facing upper and lower convex surfaces extend through a sagittal plane defined by the upper and lower vertebral processes such that the respective maximum points and the respective minimum points are disposed along the sagittal plane.

2. The intervertebral process brace of claim 1, further comprising:
    a second vertebral process support strap spanning a second portion of the frame, wherein the second vertebral process support strap is configured to engage a superior surface of the lower vertebral process and bind the lower vertebral process between the second vertebral process support strap and the second portion of the frame.

3. The intervertebral process brace of claim 2, wherein the first vertebral process support strap and the second vertebral process support strap can be tightened relative to the frame to increase a distance between the upper vertebral process and the lower vertebral process.

4. The intervertebral process brace of claim 3, wherein the frame is generally ellipse-shaped, generally C-shaped, or a combination thereof.

5. The intervertebral process brace of claim 4, further comprising:

a first vertebral process engagement structure extending from the first portion of the frame toward a center of the frame.

6. The intervertebral process brace of claim 5, further comprising:
a second vertebral process engagement structure substantially opposite the first vertebral process engagement structure and extending from the second portion of the frame toward a center of the frame.

7. The intervertebral process brace of claim 1, wherein the upper vertebral process and the lower vertebral process are spinous processes of adjacent vertebrae.

8. An interspinous process brace, comprising:
a frame configured to be installed around a first spinous process and a second spinous process, the frame comprising:
an inwardly facing upper concave surface and an opposing inwardly facing lower concave surface;
an outwardly facing upper convex surface corresponding to the upper concave surface and an opposing outwardly facing lower convex surface corresponding to the lower concave surface, the inwardly facing upper and lower concave surfaces and the outwardly facing upper and lower convex surfaces being integrally formed portions of the frame;
the upper concave surface and the upper convex surface each having respective maximum points;
the lower concave surface and the lower convex surface each having respective minimum points;
a first spinous process support strap spanning a first portion of the frame and associated with the upper concave surface;
a second spinous process support strap spanning a second portion of the frame and associated with the lower concave surface;
a locking collar attached on the first spinous process support strap; the locking collar being simultaneously movable relative to the frame and slidable along the first spinous process support strap; the locking collar operative to secure the first spinous process support strap to the frame;
wherein the first spinous process support strap and the second spinous support strap can be moved relative to the frame to increase a distance between the first spinous process and the second spinous process;
wherein when the frame is installed around the first and second spinous processes, the inwardly facing upper and lower concave surfaces and the outwardly facing upper and lower convex surfaces extend through a sagittal plane defined by the first and second spinal processes such that the respective maximum points and the respective minimum points are disposed along the sagittal plane.

* * * * *